United States Patent
Kemp et al.

(10) Patent No.: US 12,329,940 B1
(45) Date of Patent: Jun. 17, 2025

(54) DRUG DELIVERY DEVICE, ASSEMBLY FOR A DRUG DELIVERY DEVICE, METHOD FOR ASSEMBLING THE DRUG DELIVERY DEVICE AND USE OF THE DRUG DELIVERY DEVICE

(71) Applicant: Sanofi, Paris (FR)

(72) Inventors: Thomas Mark Kemp, Baldock (GB); Haiming Wu, Weston, MA (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 18/735,642

(22) Filed: Jun. 6, 2024

(51) Int. Cl.
*A61M 5/24* (2006.01)
*A61M 5/315* (2006.01)

(52) U.S. Cl.
CPC ...... *A61M 5/2422* (2013.01); *A61M 5/31501* (2013.01); *A61M 2005/244* (2013.01)

(58) Field of Classification Search
CPC .. A61M 2005/2403; A61M 2005/2407; A61M 2005/2433; A61M 2005/2437; A61M 2005/244; A61M 2205/0216; A61M 2207/00; A61M 5/24; A61M 5/2422; A61M 5/315; A61M 5/31501
See application file for complete search history.

(56) References Cited

U.S. PATENT DOCUMENTS

| | | |
|---|---|---|
| 2013/0204187 A1 | 8/2013 | Avery et al. |
| 2019/0307967 A1 | 10/2019 | Holmqvist |
| 2024/0108812 A1 | 4/2024 | Sall et al. |

FOREIGN PATENT DOCUMENTS

| | | | | |
|---|---|---|---|---|
| EA | 3448 B1 | * | 6/2003 | ............ A61M 5/178 |
| WO | WO 2004/068820 A2 | | 8/2004 | |
| WO | WO 2005/018629 A1 | | 3/2005 | |
| WO | WO 2006/003388 A2 | | 1/2006 | |
| WO | WO 2006/030220 A1 | | 3/2006 | |

OTHER PUBLICATIONS

Hamers-Casterman et al., "Naturally occurring antibodies devoid of light chains," Nature, Jun. 3, 1993, 363(6428):446-448.
Holt et al., "Domain antibodies: proteins for therapy," Trends in Biotechnology, Nov. 1, 2003, 21(11):484-490.
Muyldermans, "Single domain camel antibodies: current status," Reviews in Molecular Biotechnology, Jun. 1, 2001, 74(4):277-302.
Needle-based injection systems for medical use Requirements and test methods, Part 1: Needle injection systems, ISO 11608 1:2014(E), Third Edition, Switzerland, ISO, Dec. 15, 2014, pp. 1-13.
Ward et al., "Binding activities of a repertoire of single immunoglobulin variable domains secreted from *Escherichia coli*," Nature, Oct. 12, 1989, 341(6242):544-546.

* cited by examiner

*Primary Examiner* — Shefali D Patel
(74) *Attorney, Agent, or Firm* — Fish & Richardson P.C.

(57) ABSTRACT

A drug delivery device, comprising, an assembly comprising a circlip and a holding element, a device body; a medicament container comprising or adapted to comprise a medicament; wherein the circlip is configured in a deformed state to engage a surface of the medicament container in order to prevent relative movement in at least one direction of the medicament container with respect to the circlip; and wherein the holding element is configured to hold the circlip in the deformed state.

14 Claims, 18 Drawing Sheets

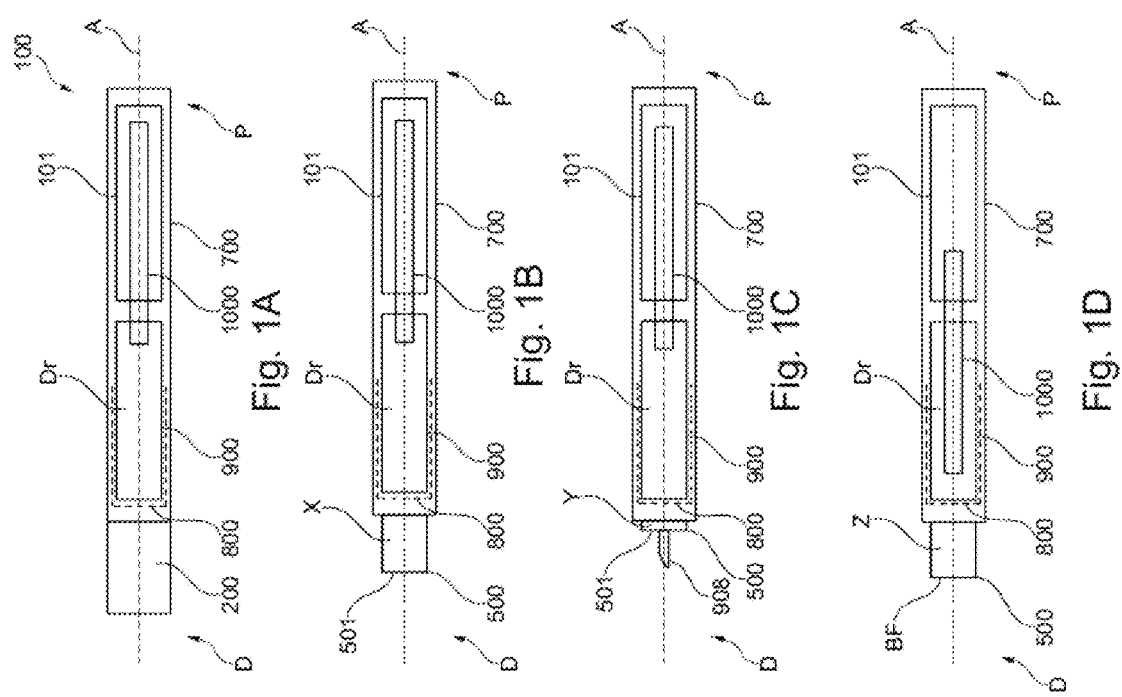

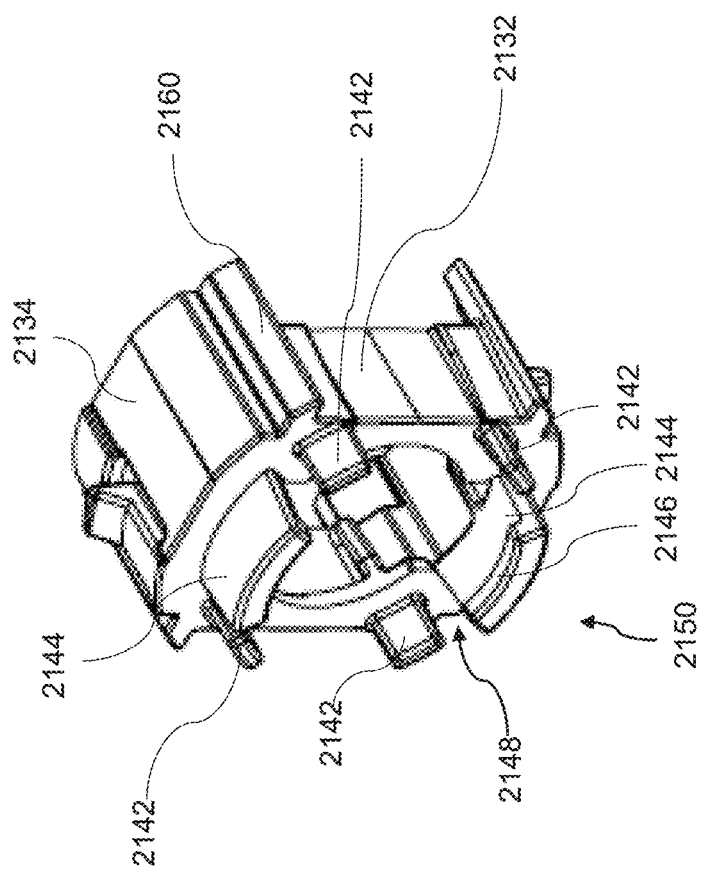

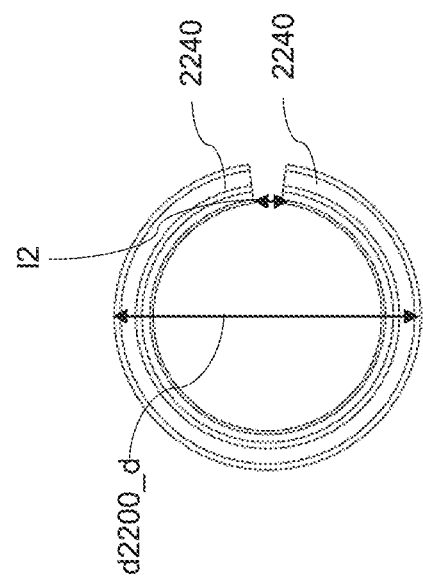
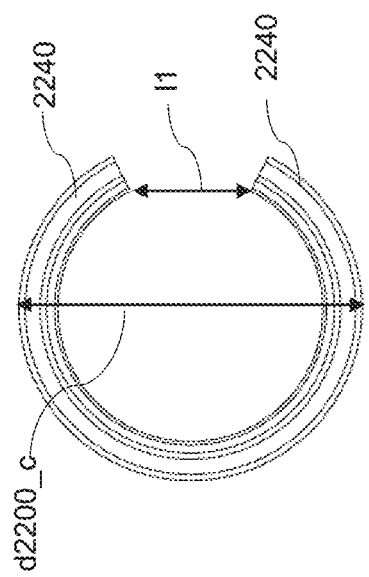
Fig. 2D

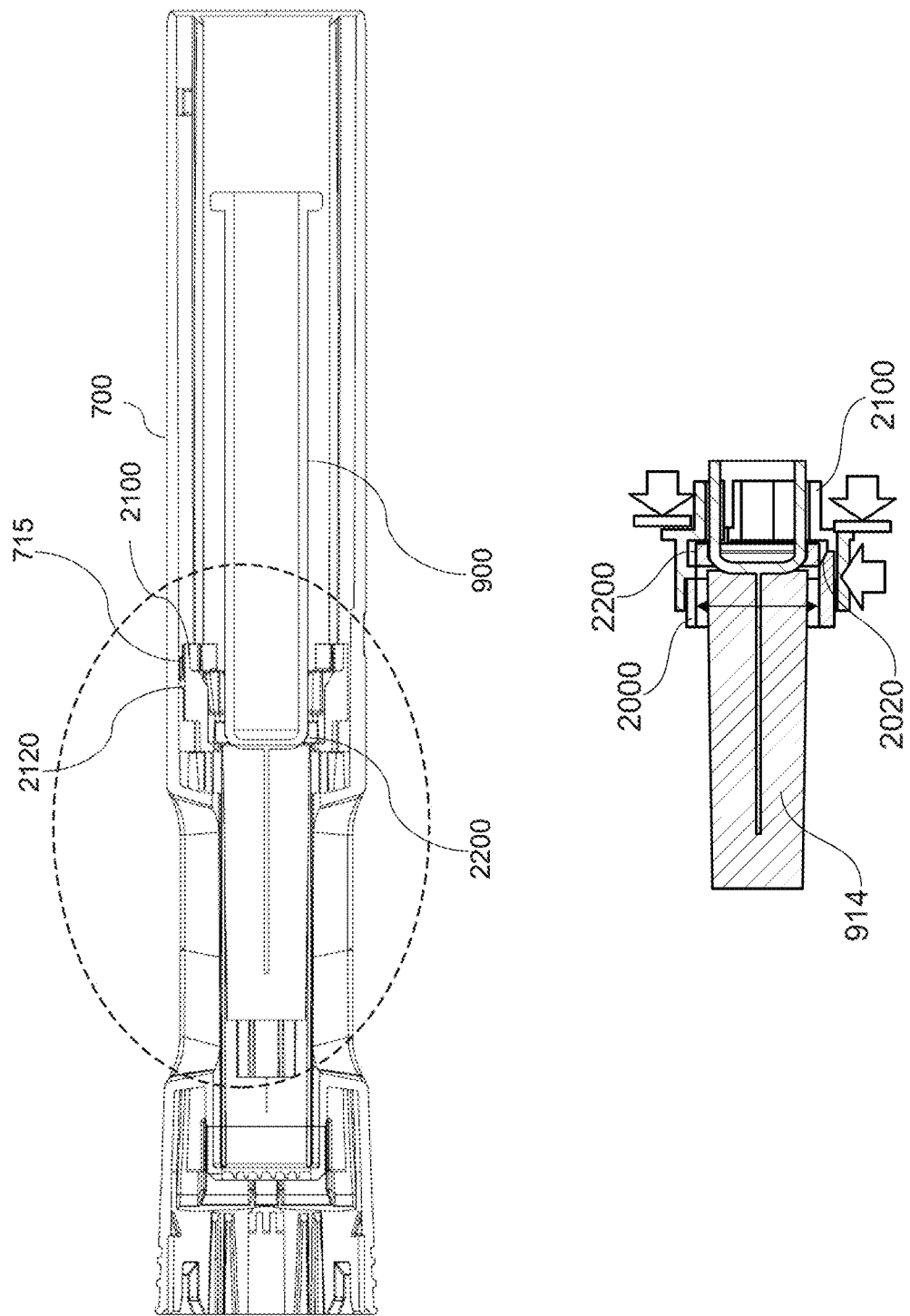

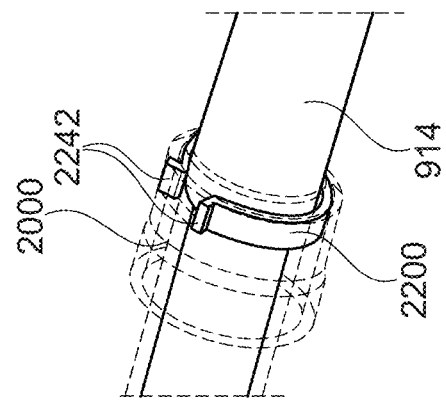
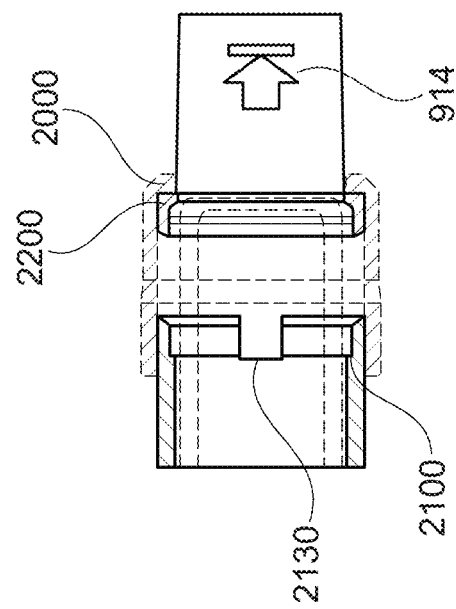
Fig. 5A

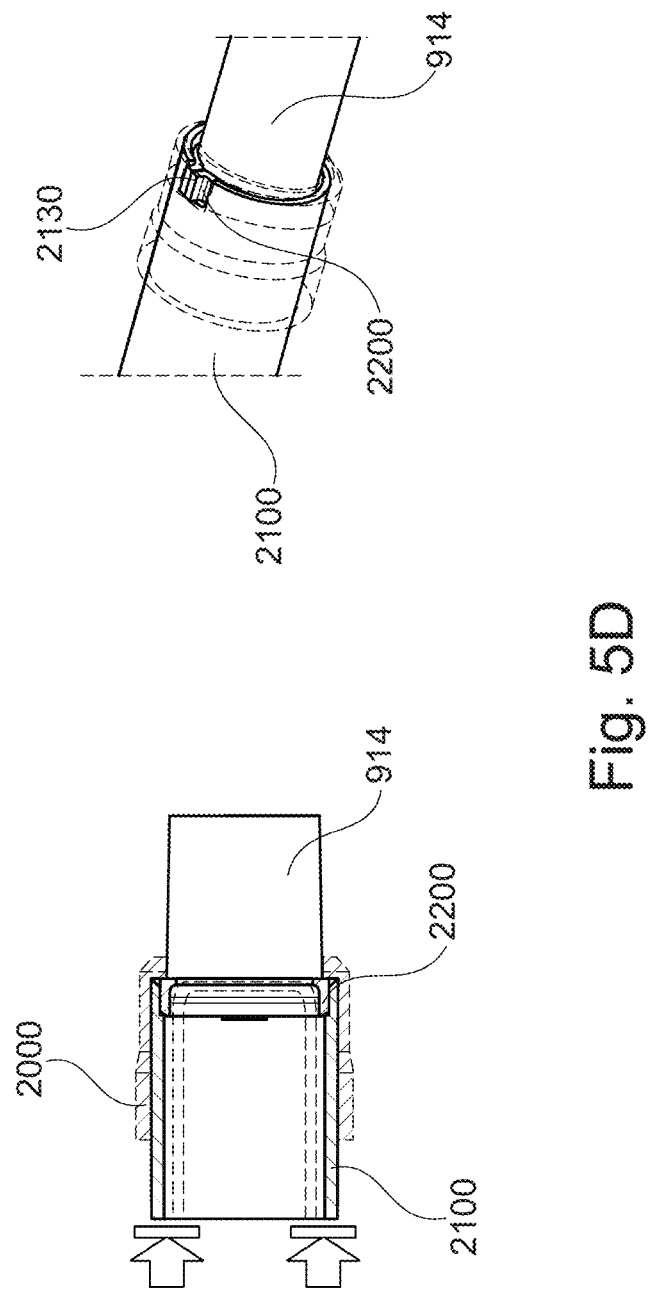

DRUG DELIVERY DEVICE, ASSEMBLY FOR A DRUG DELIVERY DEVICE, METHOD FOR ASSEMBLING THE DRUG DELIVERY DEVICE AND USE OF THE DRUG DELIVERY DEVICE

TECHNICAL FIELD

The disclosure generally relates to drug delivery device, such as an injection device, in particular an autoinjector, e.g. a reusable autoinjector, and to an assembly for a drug delivery device e.g. a drug delivery device comprising the assembly. The disclosure further relates to a method for assembling the drug delivery device and the use of the drug delivery device.

BACKGROUND

Drug delivery devices comprising a circlip configured to interact with a medicament container are known in the art. There remains, however, a need for improved assemblies.

SUMMARY

The present disclosure provides an improved drug delivery device, an improved assembly for drug delivery device as well as providing an improved method for assembling a drug delivery device.

According to a first aspect of the present disclosure a drug delivery device may be provided.

The drug delivery device may comprise an assembly. The assembly may comprise a circlip. The assembly may further comprise a holding element. The drug delivery device may further comprise a device body. The drug delivery device may further comprise a medicament container comprising or adapted to comprise a medicament.

The circlip may be configured in a deformed state to engage a surface of the medicament container. This may prevent relative movement in at least one direction, e.g. at least one axial direction, e.g. in a distal direction, of the medicament container with respect to the circlip. The holding element may be configured to hold the circlip in its deformed state.

According to at least one embodiment, the circlip may be configured to abut a proximal facing surface of the distal end of the holding element.

According to at least one embodiment, the assembly may be configured such that, if the holding element would not radially retain the circlip in its deformed state, an axial force applied to the medicament container when the circlip in its deformed state engages the medicament container, would cause an axial movement, e.g. a distal movement, of the medicament container relative to the circlip.

The medicament container during use of the drug delivery device might be subject to strong axial forces, e.g. by a drive spring. These forces may cause a disengagement of the circlip when engaged with the medicament container. The circlip might be retained in its deformed state, e.g. in a state in which it engages the medicament container, by the holding element, thereby minimizing the probability that the circlip and the medicament container move relative to each other when a strong force is applied on the medicament container.

According to at least one embodiment, the inner diameter of the distal end of the holding element is smaller than the outer diameter of the circlip in its deformed state.

According to at least one embodiment, the inner diameter of a portion of the holding element, radially delimiting the circlip, is greater than the inner diameter of the distal end of the holding element and smaller than the outer diameter of the circlip in a non-deformed state.

The drug delivery device may further comprise a viewing window. A distal end of the housing element may be arranged distally offset to the viewing window. The circlip may be arranged distally offset to the viewing window. According to at least one embodiment, wherein the holding element extends distally further distally than the viewing window and/or wherein the holding element extends further proximally than the viewing window.

According to at least one embodiment, the inner diameter of a portion of the holding element proximal to its distal end is greater than the inner diameter of the distal end of the holding element and/or smaller than the outer diameter of the circlip in a non-deformed state.

According to at least one embodiment, the assembly of the drug delivery device may comprise a stabilizing element, the stabilizing element being configured to radially stabilizes a medicament container. The stabilizing element may be arranged proximally offset with respect to the viewing window.

A proximal end of the stabilizing element may be arranged proximally offset to the proximal end of the housing element. The distal end of the stabilizing element may be arranged distally offset to the proximal end of the housing element.

According to at least one embodiment the circlip is distally offset from the stabilizing element.

According to a second aspect of the present disclosure an assembly for a drug delivery device, e.g. for a drug delivery device of the first aspect, e.g. an autoinjector, may be provided. The assembly may comprise a circlip. The assembly may comprise a holding element. The circlip may be configured to assume a first state and a second state. In the second state the diameter of the circlip might be smaller than in the first state. The assembly of the drug delivery device may be the assembly of the second aspect. The circlip and the holding element of the assembly may be the circlip and the assembly of the drug delivery device of the first aspect. Aspects of the assembly therefore may also hold for the assembly of the drug delivery device of the first aspect.

The first state of the circlip may be a non-deformed state of the circlip or the deformed state of the circlip. The second state of the circlip may be a deformed state, e.g. a radially inwardly deformed state of the circlip or a non-deformed state of the circlip.

The first state of the circlip may be a non-deformed state of the circlip and the second state of the circlip may be a deformed state, e.g. a radially inwardly deformed state of the circlip. Alternatively, the second state of the circlip may be a non-deformed state of the circlip and the first state of the circlip may be a deformed, e.g. a radially outwardly deformed state, of the circlip.

In both cases in the second state the diameter of the circlip might be smaller than in the first state. This may hold both for inner diameters and/or outer diameters of the circlip. The circlip may comprise more than one inner diameter.

The circlip may be elastically deformable, e.g. elastically deformed in its first and/or second state, e.g. the circlip might be biased to return to its previous state, e.g. in its first state, once deformed, e.g. in its second state.

The circlip in its second state may be adapted to engage a surface of a distal portion of a medicament container. Such an engagement may prevent a relative movement of the medicament container in at least one direction with respect to the circlip.

The holding element may be configured to radially restrain the circlip when in its second state, e.g. in its deformed state. Restraining radially the circlip once in its second state, e.g. in a state in which it may engage a surface of a distal portion of a medicament container, decrease the likelihood of disengagement of the circlip relative to the medicament container.

According to at least one embodiment, the assembly is configured such that an axial force applied to the medicament container, when the circlip in its second state engages the medicament container would cause an axial movement of the medicament container relative to the circlip if the holding element would not radially retain the circlip in its second state.

The medicament container during use might be subject to strong axial forces, e.g. by a drive spring. These forces may cause a disengagement of the circlip when engaged with the medicament container. The circlip might be retained in its second state, e.g. in a state in which it engages the medicament container, by the holding element, thereby minimizing the probability that the circlip and the medicament container move relative to each other when a strong force is applied on the medicament container.

According to at least one embodiment, the assembly might comprise a stabilizing element, the stabilizing element being configured to radially stabilize the medicament container. Radially stabilizing may comprise confining the possibility of a radial movement of the medicament container once the medicament container interacts with the stabilizing element. The medicament container or at least a portion of the medicament container, might not be able to move radially once it interacts with the stabilizing element.

The assembly might comprise a housing element adapted to receive at least a portion of the medicament container, e.g. a distal portion.

The stabilizing element and the housing element may be axially moveable with respect to each other. The stabilizing element and the housing element are configured such that an axial relative movement of the stabilizing element from a first relative position into a second relative position with respect to the housing element causes the circlip to assume its second state, e.g. its deformed state.

According to at least one embodiment the housing element is or comprises the holding element. The housing element, or at lest a portion of the housing element may be configured to radially restrain the circlip when in its second state, e.g. in a deformed state and biased to return to a non-deformed state.

According to at least one embodiment the housing element is configured to hold the circlip in its second state when the stabilizing element is in the second relative position relative to the housing element. The second position of the stabilizing element relative to the housing element may be a position in which the stabilizing element is nearer to the housing element than in the first relative position. In the first relative position the stabilizing element may be more proximal with respect to the housing element than in its second relative position.

According to at least one embodiment, the stabilizing element comprises a circlip receptacle. The circlip receptacle may be configured to receive the circlip in its first state, e.g. in its undeformed state, e.g. when the stabilizing element is in its first relative position relative to the housing element.

The circlip receptacle and the stabilizing element may be configured such that an axial relative movement between the circlip in its first state and the stabilizing element e.g. the circlip receptacle, is restrained when the circlip is received in the circlip receptacle. The circlip and the stabilizing element may be configured such that the circlip in its first state is at least axially confined in the receptacle area.

According to at least one embodiment, the assembly may comprise at least one interface feature. The interface feature may be configured to bring the circlip from its first state to its second state when the stabilizing element changes from its first relative position to its second relative position relative to the housing element. The housing element may comprise the at least one interface feature. The at least one interface feature may be configured as a ramp structure. When the stabilizing element changes from its first relative position to its second relative position relative to the housing element, the at least one ramp structure may be configured to interact with the circlip, e.g. in such a way as to bring the circlip from its first state to its second state, e.g. from a non-deformed to a deformed state.

According to at least one embodiment, the circlip receptacle comprises at least one slot. The at least one slot may be configured to receive the at least one interface feature, e.g. the ramp structure of the housing element. The at least one slot may be configured to receive the at least one ramp structure when the stabilizing element moves from the first relative position to the second relative position relative to the housing element.

Additionally, or alternatively the circlip may comprise at least one interface feature. The at least one interface feature may be configured as a ramp structure, e.g. the distal surface of the circlip may be configured as a ramp element. The ramp element may be configured to interact with the housing element, e.g. in such a way as to bring the circlip from its first state to its second state, when the stabilizing element changes from its first relative position to its second relative position relative to the housing element.

Both the housing element and the circlip may comprise interface feature(s). The interface features may be configured to interact with the circlip in such a way as to bring the circlip from its first state to its second state, when the stabilizing element changes from its first relative position to its second relative position relative to the housing element. The interface feature of the housing element and/or of the circlip may be configured to interact with a respective portion of the respective other element, e.g. the interface feature of the circlip may be configured to interact with the housing element and/or the interface feature of the housing element may be configured to interaction with a portion of the circlip, in such a way as to bring the circlip from its first state to its second state, when the stabilizing element changes from its first relative position to its second relative position relative to the housing element.

According to at least one embodiment, the stabilizing element may be or may comprise the holding element. The stabilizing element, or at least a portion of the stabilizing element may be configured to radially restrain the circlip when in its second state, e.g. in a deformed state and biased to return to a non-deformed state According to at least one embodiment, the housing element comprises a circlip bearing portion.

In the first relative position of the stabilizing element relative to the housing element the circlip may be arranged to abut the circlip bearing portion.

According to at least one embodiment, the stabilizing element may be configured to hold the circlip in its second state when the stabilizing element is in its second relative position relative to the housing element.

The drug delivery device of the first aspect may comprise the assembly according to the second aspect and/or any of its embodiments. The element described for one aspect may therefore correspond to the elements of the other aspect, e.g. the circlip of the assembly of the second aspect may be the circlip of the drug delivery device, the holding element of the second aspect may be the holding element of the drug delivery device.

According to a third aspect of the disclosure a method for assembling a drug delivery device, e.g. the drug delivery device of the first aspect, e.g. with the assembly of the second aspect, is provided.

The method may comprise the step of axially sliding a medicament container into a circlip.

When an axial stop surface of the medicament container, which might be configured to be engaged by the circlip, is aligned with the circlip, the method may comprise the step of bringing the circlip from a first state to a second state. In the second state the circlip may engage the axial stop surface of the medicament container in order to prevent a relative movement of the medicament container in at least one direction with respect to the circlip.

The method may comprise the step of arranging the circlip and the medicament container relative to a holding element such that the circlip may be retained in its second state via the holding element. The second state may be the deformed state.

According to a fourth aspect of the disclosure a method for using the drug delivery device, e.g. the drug delivery device of the first aspect to administer a drug is provided.

The making and using of the presently preferred embodiments are discussed in detail below. It should be appreciated, however, that the present disclosure provides many applicable concepts that can be embodied in a wide variety of specific contexts. The specific embodiments discussed are merely illustrative of specific ways to make and use the disclosed concepts, and do not limit the scope of the claims.

Moreover, same reference numerals refer to same technical features if not stated otherwise. As far as "may" is used in this application it means the possibility of doing so as well as the actual technical implementation. The present concepts of the present disclosure will be described with respect to preferred embodiments below in a more specific context namely drug delivery devices, especially drug delivery devices for humans or animals. The disclosed concepts may also be applied, however, to other situations and/or arrangements as well, e.g. for other injectors, spraying devices or inhalation devices.

The foregoing has outlined rather broadly the features and technical advantages of embodiments of the present disclosure. Additional features and advantages of embodiments of the present disclosure will be described hereinafter, e.g. of the subject-matter of dependent claims. It should be appreciated by those skilled in the art that the conception and specific embodiments disclosed may be readily utilized as a basis for modifying or designing other structures or processes for realizing concepts which have the same or similar purposes as the concepts specifically discussed herein. It should also be recognized by those skilled in the art that equivalent constructions do not depart from the spirit and scope of the disclosure, such as defined in the appended claims.

We note that features described above and below in conjunction with different embodiments or aspects can be combined with one another, even if such a combination is not explicitly disclosed herein above or below. Further features, advantages and expediencies of the disclosure and, particularly, of the proposed concepts will become apparent from the following description of the exemplary embodiments in conjunction with the drawings.

BRIEF DESCRIPTION OF THE FIGURES

For a more complete understanding of the presently disclosed concepts and the advantages thereof, reference is now made to the following description in conjunction with the accompanying drawings. The drawings are not drawn to scale. In the drawings the following is illustrated in:

FIGS. 1A to 1D a cross section of a drug delivery device according to a first embodiment and in different operating states, FIGS. 2A to 2H different views of elements of an assembly according to a first embodiment, FIGS. 3A to 3D steps showing the assembly of the assembly of FIGS. 2A to 2G into a drug delivery device according to a first embodiment of the drug delivery device, FIG. 4 a perspective view of elements of the assembly according to a second embodiment, FIGS. 5A to 5D a detailed view of steps showing the interaction between the elements of the assembly of FIG. 4 and a medicament container according to a first embodiment, and FIGS. 6A to 6D a detailed view of steps showing the interaction between the elements of the assembly of FIG. 4 and a medicament container according to a second embodiment.

DETAILED DESCRIPTION

Figure 2A:
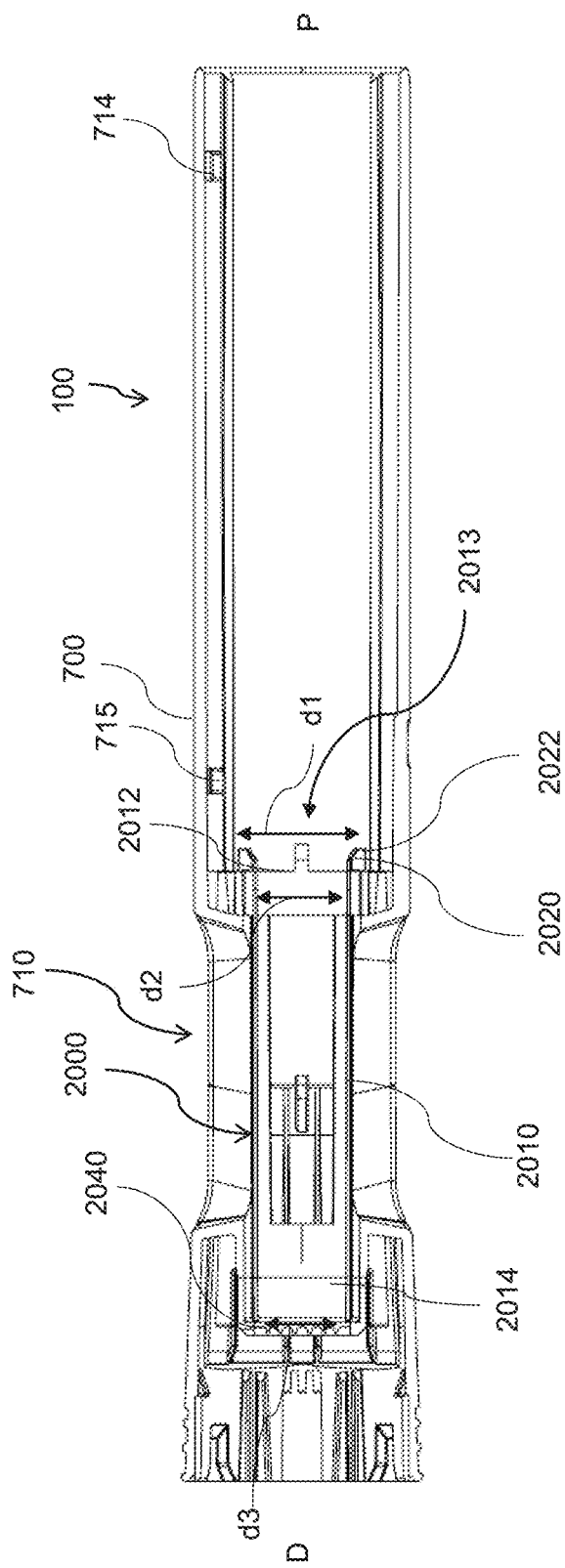

As a general note, "distal" is used herein to specify directions, ends or surfaces which are arranged or are to be arranged to face or point towards a dispensing end of the drug delivery device and/or point away from, are to be arranged to face away from or face away from the proximal end. On the other hand, "proximal" is used to specify directions, ends or surfaces which are arranged or are to be arranged to face away from or point away from the dispensing end and/or from the distal end of the drug delivery device or components thereof. The distal end may be the end closest to the dispensing end and/or furthest away from the proximal end and the proximal end may be the end furthest away from the dispensing end. A proximal surface may face away from the distal end and/or towards the proximal end. A distal surface may face towards the distal end and/or away from the proximal end. The dispensing end may be the needle end where a needle is arranged or a needle or needle unit is or is to be mounted to the device, for example. "Axial" may be used synonymously with "longitudinal".

FIGS. 1A through 1D illustrate an embodiment of a drug delivery device 100. Device 100 may be suitable as the device in the drug delivery arrangements described further above and below. The figures show device 100 in different states during its operation.

FIG. 1A illustrates the drug delivery device 100 in an initial or as delivered state. The drug delivery device 100 may comprise a device body 700. The device body 700 may be provided to retain and/or may retain a medicament container, for example a pre-filled syringe 900, in its interior. The medicament, e.g. a liquid medicament or drug Dr, may be arranged in the pre-filled syringe 900. It should be noted that the following use of the term pre-filled syringe 900 does not limit the design of the container to a pre-filled syringe.

Rather, containers other than a prefilled syringe may also be considered for implementation. The device body 700 may be provided to retain and/or may retain a needle 908, see FIG. 1C. In other words, the needle 908 may be arranged or may be arranged in the device body 700. The needle 908 can be an integral part of the pre-filled syringe 900 or container, e.g. permanently or releasable connected to a body of the medicament container, or separate from the medicament container. In the first case, the medicament container may be a syringe. In the second case, the medicament container may be a cartridge. In case a cartridge is used as medicament container, initially, the medicament container and the needle can be fluidly disconnected and fluid communication between the medicament container interior and the needle 908 may only established during operation of the drug delivery device 100. An optional medicament container carrier, such as a syringe holder 2100, may be used to support and/or carry the medicament container within the device body 700. The syringe holder may be comprised in or be part of the assembly according to at least one embodiment.

A drive mechanism 101 provided to drive a drug delivery operation may expediently be provided in the device body 700. The drive mechanism 101 may comprise a plunger 1000. The drug delivery device 100 may further comprise a drive energy source, e.g. a drive spring (not shown), such as a compression spring, (not explicitly shown). The drive energy source may be arranged to drive the plunger 1000 in a distal direction D relative to the medicament container during the drug delivery operation. During this movement, a plunger stopper (not shown), which may be movably retained in the medicament container, i.e. the pre-filled syringe 900, and may seal the medicament container, may be displaced towards an outlet of the medicament container medicament to dispense the drug Dr or medicament retained within the medicament container through the outlet. The outlet may be formed or defined by the needle 908, see FIG. 1C.

Other potential drive energy sources different from the drive spring comprise an electrical power cell or battery for driving the plunger 1000 by a motor or a reservoir suitable to provide gas pressure, where the gas pressure can be used to drive the drug delivery operation.

The drug delivery device 100 may be an autoinjector. The energy for driving the drug delivery operation in an autoinjector may be provided by components integral to drug delivery device 100 and does not have to be loaded into the device by the user during the operation of device 100 as is the case in many spring-driven pen-type variable dose injectors, where, usually, the energy is loaded into the spring by the user during a dose setting procedure.

The drug delivery device 100 may expediently be a single shot device, i.e. it is provided to dispense only one dose. The drug delivery device 100 may be a disposable drug delivery device 100, that is to say a device 100 which is disposed of after its use. The device 100 may be a pen-type device. The pre-filled syringe 900 and/or the needle 908 may be axially secured within the drug delivery device 100, e.g. within the device body 700, or may be movable relative to the device body 700, e.g. for piercing the skin. In the first case, the user may have to perform the movement for piercing the skin with needle 908. In the second case, piercing of the skin by the needle 908 may be driven by a needle insertion mechanism of the drug delivery device 100. Automatic needle retraction may be used as well.

As depicted in FIG. 1A, the drug delivery device 100 may further comprises a cap 200. The cap 200 may be arranged at a distal end DE of the drug delivery device 100. The cap 200 may be detachably connected to the remainder of device 100, e.g. the device body 700 and/or another component or member of the drug delivery device 100. The cap 200 may cover the distal end DE of the remainder of the drug delivery device 100 and/or a needle passage opening through which needle 908, e.g. a distal needle tip, may protrude to pierce the skin for the drug delivery operation. The cap 200 may comprise a needle shield remover, such as a grabber (not shown), which may engage a rigid needle shield (RNS) 914, which may cover the needle 908 such that the RNS 914 is removed from the needle 908 together with the cap 200, e.g. when the cap 200 is detached or disconnected from device 100.

The device body 700 may expediently cover the majority of the length of drug delivery device 100, e.g. 60 percent or 70 percent or more of the entire length of the drug delivery device 100 (with the cap 200 attached and/or with the cap 200 detached).

FIG. 1B illustrates the drug delivery device 100 with the cap 200 being removed. According to FIG. 1B, the device 100 may be in a state ready to be operated, e.g. ready to perform a drug delivery operation when the operation is triggered. As depicted, the drug delivery device 100 may further comprise a needle cover 500. The needle cover 500 may protrude distally from the device body 700 and/or may have been covered by the cap 200 when the cap 200 was still attached to the device body 700. The needle cover 500 may be movable relative to the device body 700 from an initial position or first position to a second position or trigger position. The needle cover 500 may be provided to extend beyond the distal tip of needle 908 which may protrude from the device body 700 before the drug delivery operation is commenced. The needle cover 500 may be movable in the proximal direction P relative to the casing 700. During this movement, e.g. before the needle cover 500 reaches the second position, the needle 908 may pierce the skin of the user.

The needle cover 500 may serve as a trigger member of the drug delivery device 100. The needle cover 500 as a trigger member, when displaced proximally from the initial or first position depicted in FIG. 1B to the second or trigger position (see FIG. 1C), may automatically initialize the drug delivery operation, preferably when it is in the second position. The drug delivery operation can be initialized by removing a mechanical lock which prevents movement of plunger 1000 in the distal direction D or by moving the plunger 1000 to disengage a mechanical lock via moving the needle cover 500. Alternatively, the needle cover 500 when moved from the first position to the second position and expediently when in the second position may only enable triggering of the drug delivery operation. In this case, a separate trigger member, e.g. a trigger button on the proximal end PE of the device body 700, may be provided to initiate the drug delivery operation. Operating the trigger button to initiate the drug delivery operation may only be possible when needle cover 500 is in the second position. In yet another alternative, the needle cover 500 may only be provided to prevent needle stick injuries before and/or after use of drug delivery device 100. In this case, the needle cover 500 may be completely decoupled from the drive mechanism 101 and/or not may be involved in triggering or enabling triggering of the drug delivery operation at all.

The needle cover 500 may be provided to bear against the skin of a user during injection. Hence, the distal surface of the needle cover 500 may provide a bearing surface or a skin contact surface. The skin contact surface 501 may delimit and/or extend around a needle passage opening provided in needle cover 500. The skin contact surface 501 may be ring-like, oval, elliptic, rectangular, quadratic, etc., circumferentially closed and/or be defined by an inward protrusion protruding radially from an inner wall of needle cover 500, e.g. a distal cylindrical portion thereof. The skin contact surface 501 may be expediently the distal end surface of needle cover 500, e.g. facing distally. The syringe with the needle may be axially fixed in the device. Needle insertion into the skin is expediently done manually and not by displacing the syringe relative to the device body 700.

FIG. 1C illustrates needle cover 500 in the second position relative to device body. This is the position when the drug delivery operation has been initiated, can be initiated, and/or when the needle 908 pierces the skin, for example. The needle 908 may protrude axially from the skin contact surface 501 of the drug delivery device 100 (particularly through the needle passage opening in needle cover 500) and, by the distance with which it protrudes over the skin contact surface 501, penetrate the skin (the skin is not shown in this representation). This distance may be characteristic for or be equal to the injection depth. The device 100 may be maintained in contact with the skin until the drug delivery operation of drug Dr has been completed, which may be indicated by an optional audible, tactile, and/or visual indication or feedback provided by the drug delivery device 100.

After the drug delivery operation has been completed, e.g. the plunger 1000 has moved distally, the device 100 may be removed from the skin (see FIG. 1D). The needle cover 500 may be biased relative to the device body 700 towards the first position by a needle cover spring 600 (not shown). Thus, when the device 100 is removed from the skin, the needle cover 500 may be moved towards the first position with respect to the device body 700. The needle cover 500 may be moved distally, e.g. beyond its first position, into a final, third or locked position relative to the device body 700. In this position the needle cover 500 may expediently be axially locked relative to the device body 700 against movement in the proximal direction P, e.g. by a locking engagement between a locking feature of needle cover 500 and the device body 700. As it is axially locked, the needle cover 500 may no longer be displaced proximally relative to device body 700 into the second position and/or into the first position. This may protect the user from needle stick injuries after use. In this state, device 100 may be locked, see FIG. 1D. The needle cover may protrude further from the device body in the third cover position Z than in the first cover position X.

FIGS. 2A to 2G show different views of elements of an assembly according to a first embodiment of the present disclosure.

The assembly might be for a drug delivery device, e.g. the drug delivery device of FIGS. 1A to 1D. The assembly might comprise a circlip 2200, and a holding element 2100 or 2000. They will be described more in detail further below.

FIG. 2A shows the holding element 2000, of an exemplary embodiment of the assembly for a drug delivery device, e.g. the drug delivery device of FIGS. 1a to 1D.

The drug delivery device 100 may comprise a device body 700. A holding element 2000 may be arranged inside the device body 700 as shown in FIG. 2A.

In this exemplary embodiment, the holding element may be a housing element 2000. In the description of FIGS. 2A to 2E, reference will be made therefore to a housing element 2000.

As will become clearer with respect to other figures, e.g. FIGS. 5A to 5D and FIGS. 6A to 6D, the disclosure is not limited to the holding element 2000 being the housing element 2000. In other embodiments, other elements of the assembly, e.g. the stabilizing element 2100, may be or may comprise to the holding element 2000.

In this exemplary embodiment the housing element 2000 is integrally formed with the device body 700. The disclosure is however not limited to this arrangement and the housing element 2000 may for example be removably attached or attachable to the device body 700.

The housing element 2000 may comprise a housing element body 2010 (in the following called "housing body 2010"). The housing body 2010 may comprise a proximal end 2012 and a distal end 2014 and may extend from the proximal end 2012 to the distal end 2014. The housing body 2010, may in this exemplary embodiment be formed as a hollow cylinder or cylindrical portion. The housing body 2010 may however also comprise other shapes.

The distal end 2014 of the housing body 2000 may correspond to the distal end of the housing element 2000. The distal end 2014 of the housing element 2000 may comprise a radially inwardly extending abutment surface 2040, e.g. a circlip bearing surface 2040 (best seen in FIGS. 3D, 5A, 6A). The circlip bearing surface 2040 may extend radially inwardly around at least a portion of the distal end 2014 of the housing element 2000, e.g. the abutment surface 2040 may be shaped as a radially inwardly extending rim 2040.

The inner diameter d3 of the distal end 2014 of the holding element, e.g. of the housing element 2000, formed by the abutment surface 2040 may be smaller than the inner diameter d2 of the housing body 2010. The circlip bearing surface 2040 may be configured as a stop element configured to stop the movement of a circlip 2200 (not shown in the figure) moved distally into the housing body 2010, as will be described later in more detail.

The inner diameter of the distal end 2014 of the housing element 2000 may be different, e.g. smaller, than the inner diameter of the housing body 2010 or at least of a portion of the housing body 2010, e.g. a portion directly proximal to the distal end.

The housing element 2000 may be adapted to receive at least a portion of a medicament container, e.g. of a syringe 900, e.g. a pre-filed syringe 900. A medicament container received in the housing element may have a proximal portion protruding proximally from the housing element 2000. A medicament container 900 received in the housing element may have a distal portion protruding distally from the housing element 2000.

The housing element 2000 may further comprise at least one interface feature 2020, e.g. a ramp structure 2020. The at least one ramp structure may extend proximally from the proximal end 2012 of the housing body 2010. The housing element 2000 may comprise more than one ramp structures, e.g. 2, 3, 4, 5, 6 or more ramp structures (in the figure, two ramp structures 2020 can be seen). If the housing element 2000 comprises more than one ramp structures, they may be arranged circumferentially around the proximal end of the housing body 2010. The at last one ramp structure 2020 may decrease in height in a proximal radially outwardly direction. The ramp structures may be arranged equidistant to each other.

Additionally, or alternatively the circlip may comprise at least one interface feature, e.g. a ramp structure (not shown).

The proximal ends 2022 of the ramp structures 2020 may be configured to form a proximal diameter d1 of the housing element 2000, e.g. a proximal diameter of the proximal end of the housing element. The proximal diameter d1 may be greater than the inner diameter of the housing body d2 and/or greater than the inner diameter d3 of the distal end d3. The ramp structures 2020 may be configured such as to narrow the diameter of the housing element 2000 between the proximal end of the ramp structures, e.g. with diameter d1, and the housing element, e.g. with an inner diameter d2 of the housing body 2001.

When attached to the drug delivery device 100, e.g. to the device body 700 and/or integral to the drug delivery device 100, the housing element 2000 may have a proximal end 2013 arranged proximally offset with respect to a viewing window 710 of the drug delivery device 100. The distal end 2014 of the housing element 2000 may be arranged distally offset with respect to the viewing windows 710 of the drug delivery device 100.

Figure 2B:
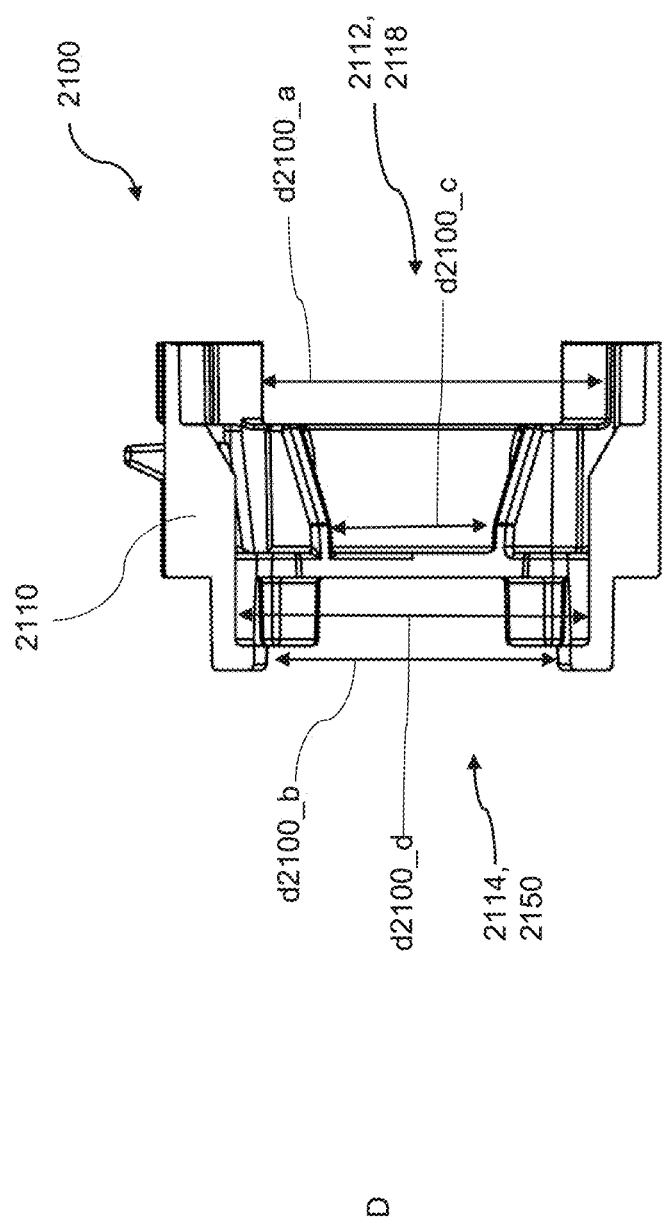

FIG. 2B shows an exemplary embodiment of a stabilizing element 2100 of an assembly according to at least one exemplary embodiment.

The stabilizing element 2100 may comprise a rear end 2112, i.e. proximal end 2012. The stabilizing element 2100 may comprise a front end 2014, e.g. a distal end. The distal 2014 may be opposite the proximal end 2112.

The stabilizing element may further define an aperture into which a medicament container, e.g. a pre-filled syringe (not shown) may be configured to be inserted. The stabilizing element 2100 may form a container receiving space 2118 into which a medicament container, e.g. a pre-filled syringe 900, may be inserted proximally e.g. into a distal direction, into the hollow cylinder formed by a stabilizing element body 2110 (herewith also called "stabilizing body 2110").

The stabilizing element 2100, may comprise a circlip receptacle 2150. A distal portion of the stabilizing element 2100 may define the circlip receptacle 2150. The circlip receptacle 2150 may be configured to receive a circlip 2200 arranged in the circlip receptacle, e.g. in a first state of the circlip 2200 as will be described later in FIGS. 2F and 2G in more detail.

The stabilizing element 2100 may comprise at its proximal end a first inner diameter $d2200\_a$. The stabilizing element 2100 may comprise at its distal end a second inner diameter $d2200\_b$.

The stabilizing element 2100 may comprise in a stabilizing body portion a third inner diameter $d2200\_c$. The first inner diameter $d2200\_a$ may be greater or equal than the second inner diameter $d2200\_b$ and/or than the third inner diameter $d2200\_c$. The second inner diameter $d2200\_b$ might be greater or equal than the third inner diameter $d2200\_c$. The third inner diameter $d2200\_c$ may for example be the minimal inner diameter of the stabilizing element 2100. The second inner diameter $2200\_b$ might for example be smaller than the outer diameter of the circlip 2200 in its first state.

FIG. 2C shows a perspective view of the stabilizing element 2100 of the previous figure. The stabilizing element 2100, may be non-circular, e.g. comprise two rounded sections 2134 arranged oppositely, e.g. diametrically opposite, to each other and two in a radial inward direction recessed sections 2132 being flatter than the rounded sections 2134. As such the two rounded sections extend circumferentially as semicircles. The two recessed sections may be arranged at the other opposite, e.g. diametrically opposite, ends of the stabilizing element 2100 and on opposite sides of the stabilizing element 2100 with respect to the rounded sections 2134. The two recessed sections 2132 may define a recessed outer surface.

The edges between the rounded sections 2134 of the stabilizing element 2100 and the flat recesses of the stabilizing element 2100 may also comprise or form guiding features 2160, for aiding the positioning of the stabilizing element 2100 into the device body during assembly. In other words, the stabilizing element 2100 may comprise guiding features 2160 extending along the longitudinal axis on the stabilizing element 2100, the guiding features 2160 being arranged on the sidewalls of the stabilizing element 2100 delimiting the space defined by the recessed sections 2132.

The stabilizing element 2100 may comprise at least one circlip holding arm 2144. In this example the stabilizing element comprises two circlip holding arms 2144. The circlip holding arms 2144 may be flexible. The circlip holding arms 2144 may protrude inwards in a relaxed state. Alternatively, the circlip holding arm 2144 may be protruded outwards in a relaxed state. Other configurations of the arms in the relaxed state are also possible.

The circlip holding arms 2144 may have the same width throughout their extension. i.e. the wideness of a one circlip holding arm 2144 at its proximal end corresponds to the wideness of the circlip holding arm 2144 at its distal end.

The circlip holding arms 2144 may extended distally from the stabilizing element body 2110 and may be protruded inwards in a relaxed state, e.g. are inwardly formed, e.g. angled. The circlip holding arms 2144 may comprise at its distal ends a circlip holding arms protrusion 2146 that may be directed radially, e.g. radially inwardly.

The circlip holding arms protrusion 2146 may comprise on their proximally facing surface ramps decreasing in height in a proximal direction, which aid the assembly process as described in more detail later on with respect to other figures The stabilizing element 2100 may further comprise at least one, two or more, e.g. four as in this example, circlip receptacle delimiting members 2142. The circlip receptacle delimiting members 2142 may be shaped, respectively, as protrusions extending distally from the stabilizing element 2100. The axial extension of the circlip receptacle delimiting members 2142 may correspond to the axial extension of the circlip holding arms 2144. Alternatively, the axial extension of the circlip receptacle delimiting members 2142 may be less than the axial extension of the circlip holding arms 2144. The circlip receptacle delimiting members 2142 may extend axially parallel to the circlip holding arms 2144.

The circlip receptacle 2150 may be radially delimited by the (radially) inner surfaces of the circlip holding arms 2146 and of the circlip receptacle delimiting members 2142. Distally the circlip 2200 receptacle may be delimited by the proximally facing surface of the circlip holding arms protrusion 2146. Proximally the circlip receptacle 2150 may be delimited by the stabilizing body 2110.

The circlip receptacle 2150 may be configured to receive the circlip 2200, e.g. in a non-deformed state.

The circlip receptacle delimiting members 2142 and/or the circlip holding arms 2144 may be configured to prevent a radial movement of the circlip 2200 out of the circlip receptacle 2150.

The circlip holding arms protrusion 2146 may be configured to at least partially prevent movement of the circlip 2200 in an axial, e.g. a distal direction, when the circlip 2200 is arranged in the circlip receptacle, e.g. in its first state.

The stabilizing body 2110 may be configured to partially prevent movement of the circlip 2200 in an axial, e.g. a proximal direction, e.g. out of the circlip receptacle 2150, when the circlip is arranged in the circlip receptacle 2150, e.g. in its first state.

The circlip receptacle 2150 may have a substantial round or oval shape. The diameter of the circlip receptacle d2100_d (see FIG. 2B) may be greater than the outer diameter of the circlip 2200 in its first state.

The circlip receptacle delimiting member 2142 may or may not comprise circlip holding arms protrusion(s) similar to the circlip holding arms 2144.

The circlip holding arms 2146 and the circlip receptacle delimiting member 2142 may together form or define slots 2148. The slots 2148 may be defined by the circumferential space between each circlip receptacle delimiting member 2142 and its neighboring circlip holding arm 2144. The axial extension of the slots 2148 may be given by the axial extension of the circlip receptacle delimiting member 2142 and/or of the circlip holding arms 2144.

The slots 2148 may be configured such as to be able to receive the interface feature, e.g. the ramp structure of the housing element 2000. The slots 2148 may be substantially as wide as the ramp structures 2020 of the housing element 2000.

On its radially outwardly facing surface the stabilizing element 2100, e.g. the rounded section 2134 may comprise at least one holding clip 2120 for releasable intermittent holding of the stabilizing element 2100 relative to the device body 700. The holding clips 2120 may be integrally formed on the rounded section 2134 as tongues or clips. In particular, the holding clips 2120 may have a flexible portion, which substantially extends in the axial direction and which is deflectable in the radial direction.

Proximal ends of the holding clips 2120 may be radially outwardly directed to engage cut-outs (not shown) of device body 700. In one embodiment, the proximal ends may have an inclined surface with a radial outward inclination in the proximal direction P. In an embodiment, the stabilizing element 2100 may comprise two holding clips 2120 arranged opposite to each other. Instead of cut-outs, the device body 700 may comprise an inner support to releasable hold the holding clips 2120. In particular, the inner support may be formed as an inner groove.

The holding clips 2120 may be configured such that in a first engaged position of the stabilizing element 2100, the holding clips 2120 interact with slots, e.g. first cut-outs of the device body 700. In the first engaged position, the stabilizing element 2100 may be moved distally, but may be prevented from moving proximally relative to the device body 700, thereby exiting the device body 700. For example, this can be achieved for example through a ramped distal surface of the holding clips 2120, e.g. a ramp which increases in height in its proximal direction. Further, in the first engaged position, the stabilizing element 2100 may be prevented from rotating relative to the device body 700.

The holding clips 2120 may be configured such that, when the stabilizing element 2100 is moved distally, e.g. during its assembly process, the holding clips 2120 disengage from the first cut-outs 714. A further distal movement of the stabilizing element 2100 re-biases the holding clips 2120 radially inwards until the holding clips 2120 align with distal slots, e.g. the second (distal) cut-outs of the device body 700. Upon alignment, the holding clips 2120 interact with the second cut-outs 715 by deflecting radially outwardly into the space formed by the second cut-outs 715. This is the second engaged position of the stabilizing element 2100. The interaction between the holding clips 2120 and the second cut-outs prevents a proximal movement as well as a rotational movement of the stabilizing element 2100 relative to the device body 700.

FIG. 2D shows an exemplary embodiment of a circlip 2200 in its first state (left) and second state (right).

The circlip 2200 may be configured to assume the first state and the second state. In the second state the diameter of the circlip might be smaller than in the first state. If not otherwise noted, when discussing the diameter of the circlip, the outer diameter is intended. The circlip in its second state might be adapted to engage a surface of a distal portion of the medicament container, e.g. of the syringe 900, in order to prevent a relative movement of the medicament container in at least one direction with respect to the circlip.

The circlip 2200 may have a ring shape with open ends, e.g. with two arms 2240, e.g. a C-shape or a U-shape.

The arms 2200 in a first state may be at a distance l1 from each other. The circlip 2200 in its first state may have a first outer diameter d2200_c. The first state may correspond to a non-deformed state of the circlip 2200.

In the second state the circlip 2200 may be in a deformed state, e.g. a state in which a second outer diameter d2200_d is smaller than the first outer diameter d2200_a in the first state. The distance l2 between the arms 2240 in the second state may be smaller than the distance l1 in the first state.

The circlip 2200 may be elastically deformable, i.e. once in the second state, the circlip 2200 would return to the first state if not constrained by any force.

Figure 2E:
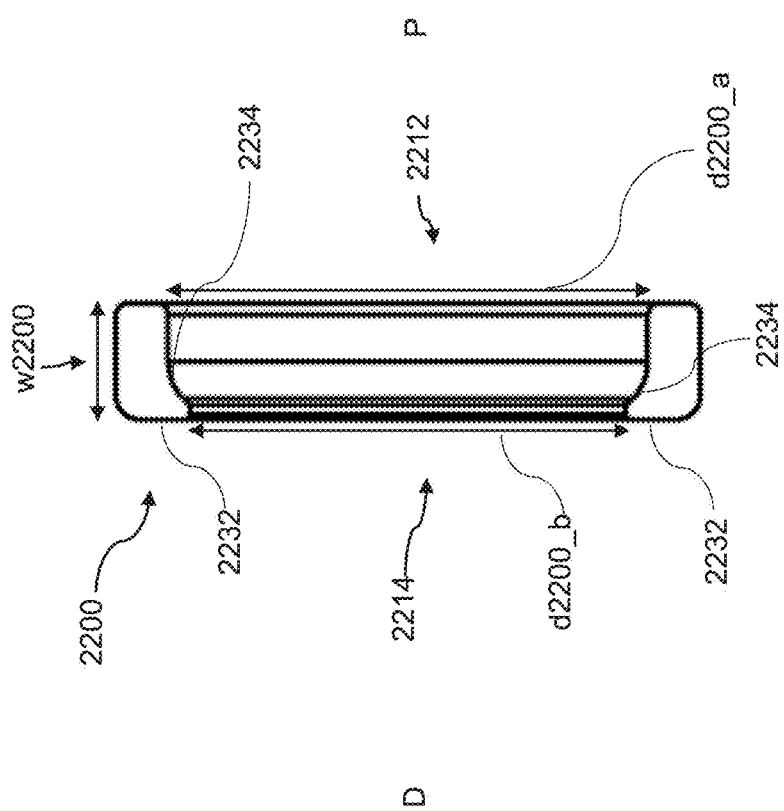

FIG. 2E shows a cross sectional view of the circlip 2200 of the assembly according to an exemplary embodiment. The circlip may comprise a proximal end 2212 and a distal end 2214 opposite the proximal end 2212. The circlip 2200 may be adapted to receive at least a portion of a medicament container, e.g. of a pre-filled syringe.

The proximal end 2012 of the circlip 2200 may comprise a first inner diameter d2200_a, e.g. a proximal inner diameter d2200_a. The distal end 2214 of the circlip 2200 may comprise a second inner diameter d2200_b, e.g. a distal inner diameter d2200_a. The second inner diameter d2200_b may be smaller than the first inner diameter d2200_a. The circlip 2200 may extend axially for a width w2200. The width w2200 may be more or equal than 1 mm, 2 mm, 3 mm, 4 mm, 5 mm, 6 mm, 7 mm. The width w2200 may be less or equal than 8 mm, 7 mm, 6 mm, 5 mm, 4 mm, 3 mm. The width w2200 of the circlip 2200 may be less or equal than a third of the width of the stabilizing element 2100. The width w2200 may for example be less than a fourth of the width of the stabilizing element 2100.

The circlip 2200, e.g. the distal end 2114 of the circlip 2200 may further comprise a proximally-facing contoured surface 2234. The contoured surface 2234 may be configured to accommodate a surface portion of a medicament container, e.g. a proximal portion of a neck portion of a syringe 900, as will be described more in detail with reference to other figures. The contoured surface 2234 may extend radially inwardly The circlip 2200, e.g. the distal end 2214, may also comprise distally-facing planar surfaces 2232. The distally-facing planar surface may be configured to at least partially abut the needle shield 914 of a syringe 900 and/or to at least partially abut the abutment surface 2040, e.g. the circlip bearing surface of the housing element 2000.

Figure 2G:
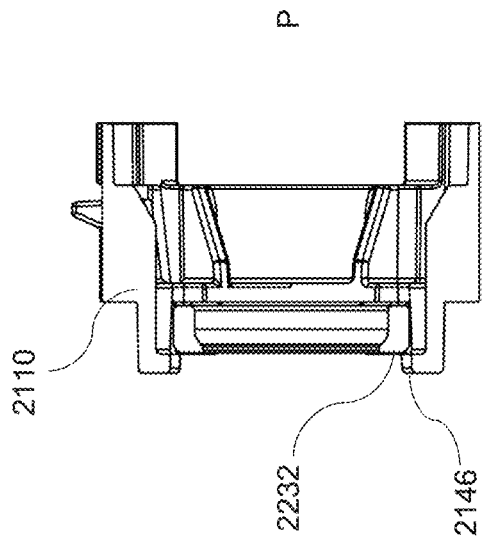
Figure 2F:
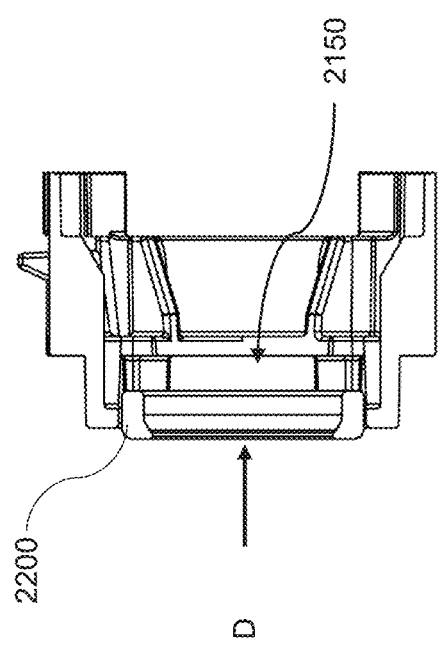

FIG. 2F and FIG. 2G show an exemplary step in which a circlip 2200, e.g. the circlip of FIGS. 2D and 2E is assembled onto the stabilizing element 2100, e.g. into the circlip receptacle 2150, e.g. of stabilizing element 2100 of FIGS. 2b and 2C.

The circlip 2200 may be received distally into the circlip receptacle 2150. The step may comprise deforming the circlip 2200 from its first state to a first prime state. In the first prime state the circlip 2200 may be deformed to have an outer diameter smaller than the second inner diameter d2100_b of the stabilizing element 2100. This may allow the insertion of the circlip 2200 into the circlip receptacle 2150. The circlip 2200 may be elastically deformable. Once arranged in the circlip receptacle 2150 the circlip 2200 may return to its first state, e.g. to a non-deformed state.

In the circlip receptacle 2150 the circlip 2200 may be restrained from radial outwardly movement outside of the circlip receptacle by the inner surfaces of the circlip holding arms 2146 and of the circlip 2200 receptacle delimiting members 2142. The circlip 2200 may be restrained from any distal movement outside of the circlip by the circlip holding arms protrusion 2146, e.g. their proximally facing surface. The distally facing planar surface of the circlip 2200 may abut the proximally facing surface of the circlip holding arms protrusion 2146. The circlip 2200 may be restrained from any proximal movement outside of the circlip by the stabilizing element body 2110.

Figure 2H:
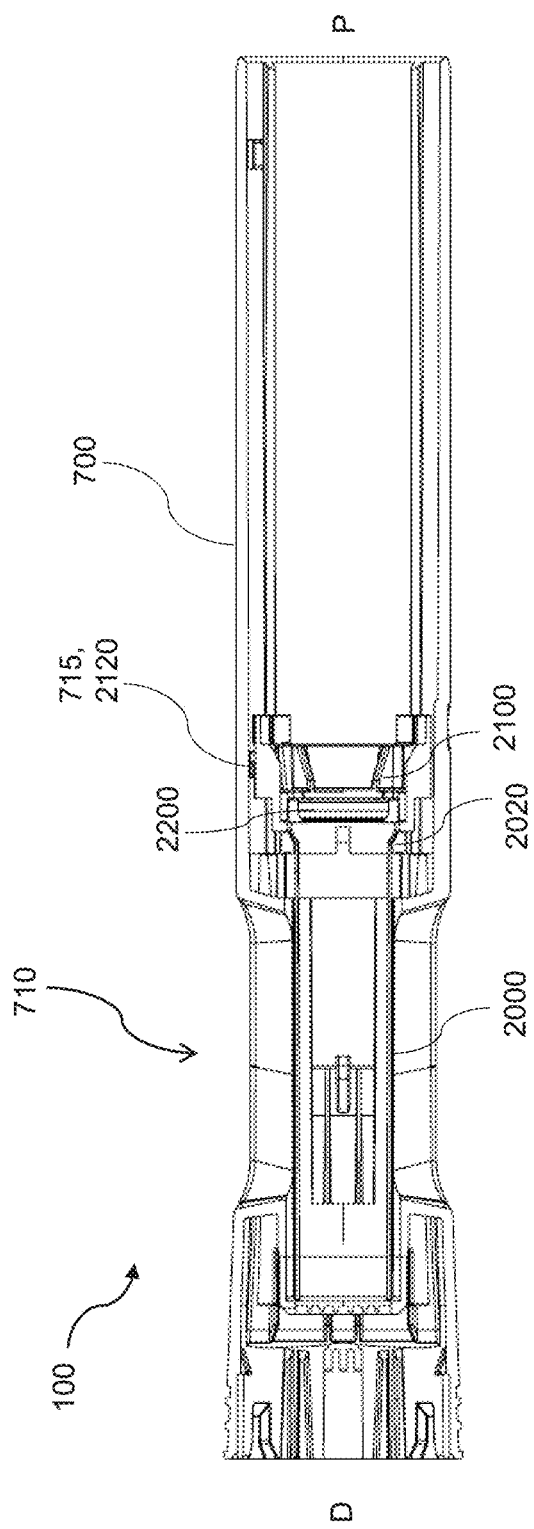

FIG. 2H shows a stabilizing member 2100, e.g. the stabilizing member 2100 of FIGS. 2B and 2C, with a circlip 2200, e.g. the circlip of FIGS. 2D and 2E arranged in its first relative position with respect to the holding element 2000 (e.g. housing element 2000 of FIG. 2A) in a drug delivery device 100.

As can be seen from the figure, in its first relative position the stabilizing element 2100 may be arranged proximally offset with respect to the housing element 2000, e.g. proximally with respect to the proximal end of the housing element 2000. The stabilizing element 2100 in its first relative position may be releasable axially fixed with respect to the device body 700 of the drug delivery device 100 by the clip 2120 interacting with the cut-out 715 of the device body 700, as described above. A force in the distal direction applied to the stabilizing element 2100 might cause a disengagement of the stabilizing element 2100 with respect to the device body 700, e.g. a disengagement of the clip 2120 with respect to the cut-out 715. In this first relative position the medicament container might be partially inserted into the stabilizing element 2100 and/or into the housing element 2000 (not shown).

As can be seen, in the first relative position the stabilizing element 2100 and/or the circlip 2000 may be proximally offset with respect to the proximal end of the viewing window 710 of the drug delivery device 100.

The ramp structure 2020 of the housing element 2000 may at this stage not interact with the stabilizing element 2100, e.g. with the slots 2148 of the stabilizing element 2100.

FIGS. 3A to 3D show an exemplary first embodiment of assembly steps of a drug delivery device 100. The stabilizing element 2100 in the schematic representations of the figures has a slightly different shape than the one in FIGS. 2A to 2H. The steps of FIG. 3A to 3D however work similarly with respect to the stabilizing element 2100 embodiment of the previous figures. The differences in form are only with respect to portions which might not be relevant for the explanation of the steps of the following figures. The disclosure is not limited to the stabilizing element shown in FIGS. 3A to 3D.

In the figures a pre-filled syringe 900 is shown. The exemplary steps are however not limited to a pre-filled syringe 900 and other medicament containers may be used.

In FIGS. 3A to 3D, the syringe 900 may comprises a needle shield 914, e.g. a rigid needle shield 914 adapted to cover a needle 908. The rigid needle shield 914 of this embodiment has substantially the same diameter as a barrel 901 of the syringe 900. The needle shield may however also comprise different diameters than the barrel 901, e.g. a greater diameter or a smaller diameter.

The syringe 900 may comprise a drug dr. At its proximal end the syringe 900 may comprise a flange 912. The distal end of the barrel 901 may comprise a needle 908 which extends distally. The needle 908 may be covered by the needle shield 914, e.g. the rigid needle shield 914.

Between the barrel 901 of the syringe 900 and the needle shield 914 covering the needle 908 of the syringe 900, in a neck portion of the syringe, a circumferential gap 904 may be formed.

Prior to the steps described in the FIGS. 3A to 3D, the stabilizing element 2100 together with the circlip 2200 may have been inserted into the drug delivery device 100 and may have been arranged with respect to the housing element 2000 as shown in FIG. 2H.

Figure 3A:
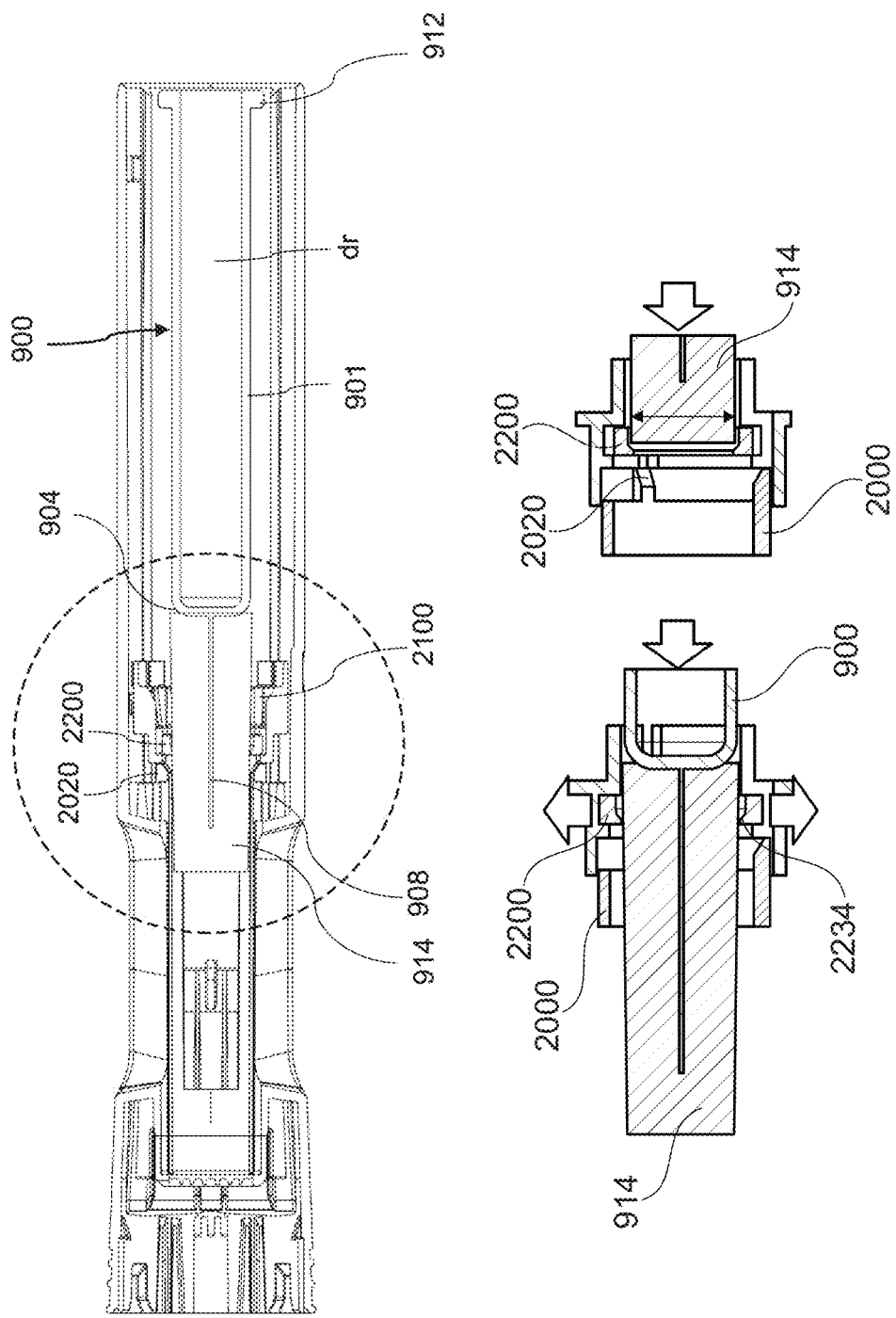

As shown in FIG. 3A, the syringe 900 is partially inserted into the device body 700 of the drug delivery device 100. In particular the syringe 900 is at least partially inserted such that the rigid needle shield 914 is at least partially received by the housing element 2000 and/or the stabilizing element 2100 and/or the circlip 2200.

As can be seen in the schematic view of FIG. 3A, the syringe 900 may be inserted from the proximal side, distally into the stabilizing element 2100. The syringe 900 may be moved further distally such as to bring into contact the rigid needle shield 914 with the circlip 2200. The radially contoured surface 2234 of the circlip 2200 may be configured such that a further distal movement of the syringe 900 relative to the stabilizing element 2100 causes a radially outwardly deformation of the circlip 2200 from its first state, e.g. such that it causes an increase in diameter of the circlip 2200 with respect to the diameter in its first state.

Such a deformation may be caused by the rigid needle shield 914 having a greater diameter than the circlip 2200 in its first state, e.g. in its state in which it is arranged in the stabilizing element 2100, e.g. in which it is arranged in the circlip receptacle 2150, prior to insertion of the syringe 900 (see previous figures). The diameter of the rigid needle shield may be equal or smaller than the proximal inner diameter d2200_a of the circlip 2200. This may allow the proximal insertion of the syringe 900 into the circlip 2200. The diameter of the rigid needle shield may be greater than the distal inner diameter d2200_b of the circlip 2200. This may cause the radial outward deformation of the circlip 2200 when the rigid needle shield 914 passes the distal end 2214 of the circlip 2200.

When the rigid needle shield 914 passes the circlip 2200 it may therefore deform the circlip 2200 in a radially outwardly direction such as to increase its diameter, as shown by the arrows pointing in an outwardly radial direction. The increase in diameter may therefore allow the rigid needle shield 914 to completely pass the circlip 2200 (as will be shown in the next figures).

The circlip 2200 in this example is elastically deformable. The circlip 2200 when deformed radially outwardly would therefore tend to return to its first state. As such the circlip 2200 may apply a radially inwardly force on the rigid needle shield 914 of the syringe 900, when the rigid needle shield is moving through the circlip 2200. The circlip 2200 may be configured such that the radial inwardly force applied by the circlip 2200 on the rigid needle shield 914 is small enough to permit movement, e.g. distal movement, of the needle shield 914 e.g. without damaging the rigid needle shield 914.

During assembly, a user may receive a tactile feedback of the relative position of the syringe 900, e.g. of the rigid needle shield 914, with respect to the circlip 2200, due to the necessity of increased forces required to push the syringe, e.g. distally, into and/or through the circlip, once the rigid needle shield 914 may have abutted the circlip.

During this step, the circlip might still be located in the circlip receptacle 2150. The circlip receptacle may be configured such as to allow the radial outwardly deformation of the circlip 2200. The circlip holding arms 2144, the circlip receptacle delimiting members 2142 and/or the circlip holding arms protrusion 2146 may be configured such that a deformation of the circlip 2200 in a radially outwardly direction is at least partially possible.

The circlip holding arms 2146 and/or the circlip holding arms protrusion 2144 may be configured such as to restrict a distal movement of the circlip 2200 once it engages the rigid needle shield 914, e.g. once the rigid needle shield comes into contact with the circlip 2200 and moves further distally thereby increasing the circlip's diameter, as described above. This may guarantee that during this assembly step the circlip 2200 may remain in the circlip receptacle 2150.

The distal movement of the syringe 900 may be achieved by specific tools or manually.

Figure 3B:
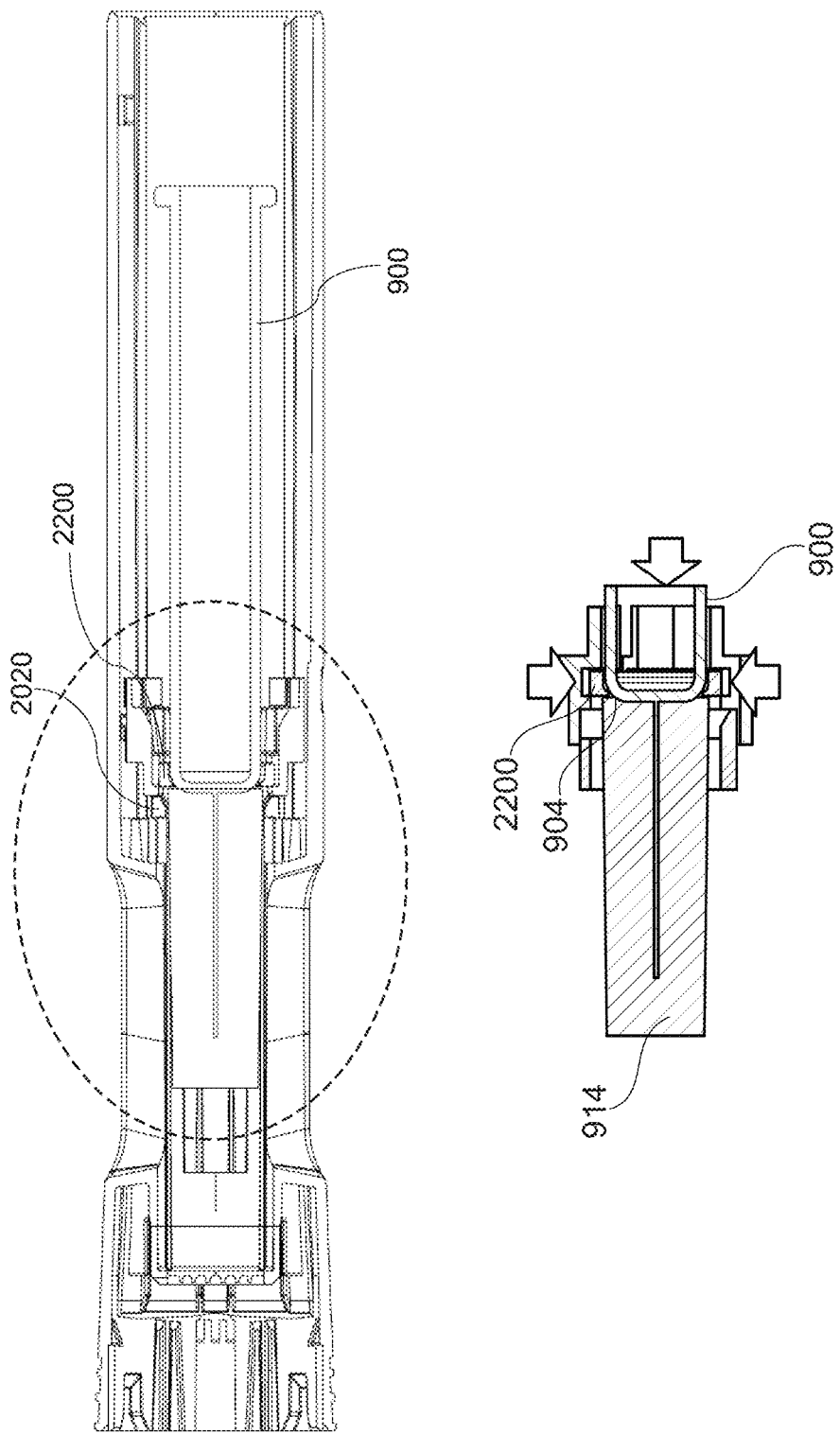

FIG. 3B shows a further exemplary assembly step. In FIG. 3B the syringe 900 may be moved further distally until an axial stop surface of the medicament container, which might be configured to be engaged by the circlip, is aligned with the circlip, e.g. until the circumferential gap 904 is aligned, e.g. radially aligned, with the circlip 2200. Before alignment occurs, the circlip 2200 may still be biased towards its first state, e.g. the circlip 2200 may be in its state with a wider diameter than in the first state but would tend to return to its first state.

Once alignment with the circumferential gap 904 occurs, the circlip 2200 might return to its first state, e.g. by deforming radially inwardly, as shown by the respective arrows pointing radially inward. The circlip 2200 may return to its first state and be at least partially received in the circumferential gap 904. The distal facing surface of the circlip 2200 may abut the rigid needle shield. The contoured surface may be such as to follow at least partially the contour of the barrel 901 of the syringe 900. The circlip 2200 may therefore be engaged to the syringe 900.

The engagement of the circlip to the syringe 900 may be such that an assembly force applied on the syringe to push the syringe axially, e.g. distally, would result in a corresponding movement of the circlip 2200 in the same direction, e.g. distally.

The engagement of the circlip to the syringe 900 may be such that an operation force applied on the syringe during operation of the drug delivery device, would result in a disengagement of the circlip to the syringe, e.g. in an axial move of the syringe relative to the circlip 2200. The operation force may be greater than the assembly force.

Figure 3D:
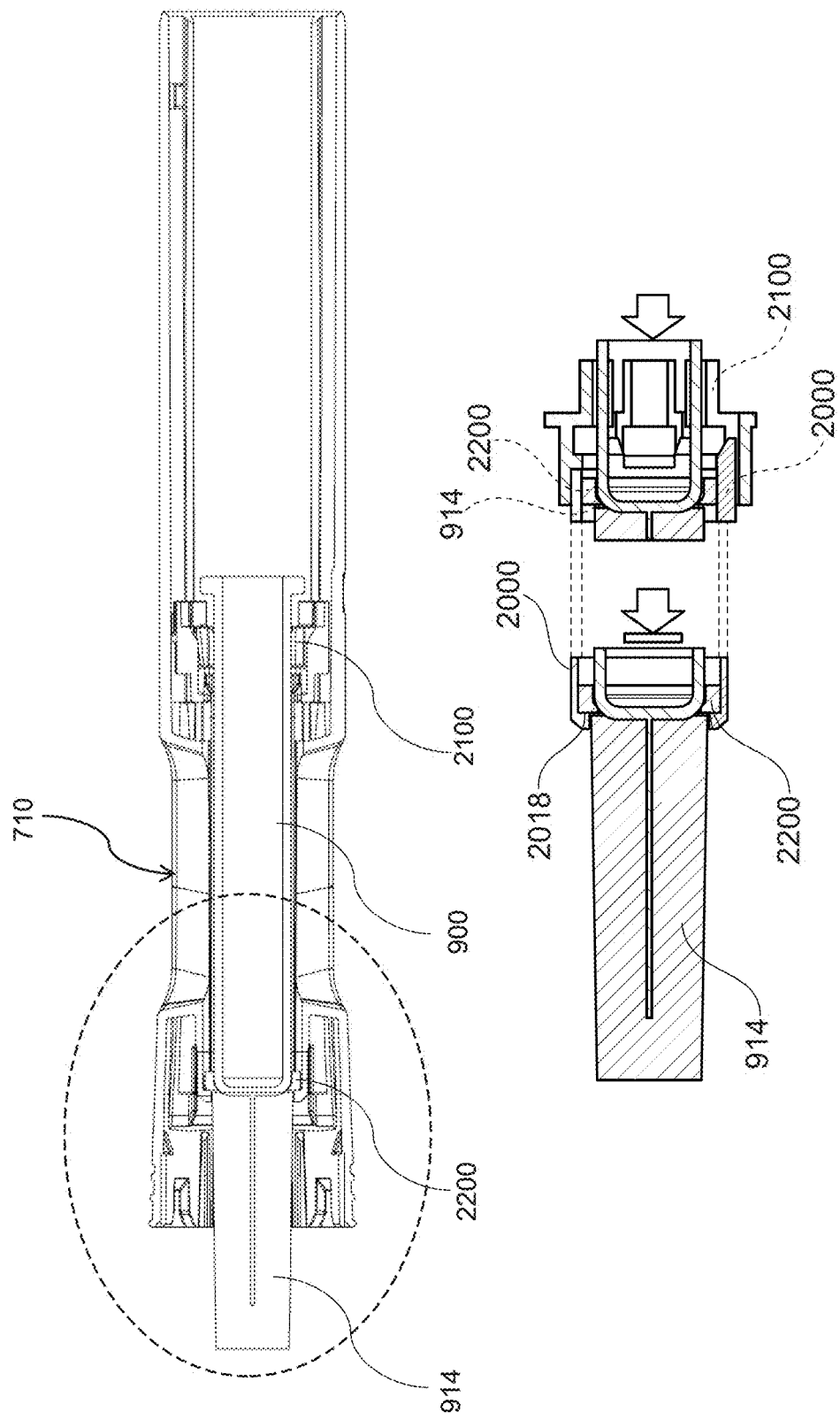

The assembly force may be the force with which the syringe is moved further distally during the next assembly steps, e.g. the step shown in FIG. 3D. The operation force may be the force exerted on the syringe 900 during operation of the drug delivery device 100.

FIG. 3C shows a further exemplary assembly step. In this step the stabilizing element 2100 is moved, e.g. pushed distally.

A distal force applied on the stabilizing element 2100 may release the clip element from the cut out 715 of the device body 700. This may release the stabilizing element 2100 from its axially locked position relative to the device body 700 and allow its further distal movement.

An axial relative movement of the stabilizing element 2100 from a first relative position into a second relative position with respect to the housing element 2000 may cause the circlip 2200 to assume a second state, e.g. a deformed state.

The circlip 2200 may be still arranged in the circlip receptacle 2150. An axial, e.g. a distal, movement of the stabilizing element 2100 may therefore correspond to an axial, e.g. distal, movement of the circlip 2200. The circlip may be engaged to the syringe 900 in the circumferential gap 904 as for example described with respect to FIG. 3B. The circlip 2200 may be in its first state.

The axial force applied to the stabilizing element 2100 and thereby to the circlip 200 maybe such that a distal movement of the stabilizing element 2100 correspond to the same distal movement of the syringe 900. The axial force may correspond to the assembly force.

The stabilizing element 2100 and the housing element 2000 may be configured such that distal movement of the stabilizing element 2100 with respect to the housing element 2000 causes the ramp structures 2020 to slide into the slots 2148 of the stabilizing element 2100.

The circlip 2200 may interact with the interface feature 2020, e.g. the ramp structures 2020 due to the ramp structures 2020 being received in the slots 2148. The ramp structures 2020 may be configured such that the circlip 2200, interacting with the ramp structure 2020 is deformed into its second state. The ramp structures 2020 are configured such that their insertion into the slots 2148 cause a radially inwardly force acting on the radial surface of the circlip 2200. This may cause the circlip 2200 to deform, e.g. in its second state, e.g. with a diameter smaller than in the first state. In other words, the circlip 2200 moving distally may interact with the ramp structures 2020 such that the diameter of the circlip 2200 is decreased. The circlip 2200 in its second state may have an inner diameter being smaller than the outer diameter of the rigid needle shield 914.

Embodiments in which the interface feature may be configured additionally or alternatively on the circlip 2200, the mechanism is similar, e.g. the interface feature(s) of the circlip may be configured to interact with a portion of the housing element 2000 such as to bring the circlip from its first state to its second state as described above.

The circlip 2200 before its change into the second state may have been engaged to the syringe in the circumferential gap 904 as explained above. The engagement of the circlip 2200 with the syringe 900 may be such as to allow a further decrease in diameter of the circlip 2200. In other words, the circlip 2200 in the circumferential gap 904 may have enough space to further deform in a radially inwardly direction.

A decreased diameter, e.g. the circlip 2200 being in its second state, may increase the contact of the circlip 2200 with the barrel 901 the syringe 900. This may further increase the engagement of the circlip 2200 with the syringe 900, e.g. with the barrel 901 of the syringe 900.

The move of the stabilizing element 2100 in a distal direction as described in relation to FIG. 3C may be achieved via an external tool, e.g. a press head.

The distal movement of the stabilizing element 2100 may occur until the distally facing surface of the circlip holding arms protrusion 2146 abuts a proximally facing surface of the housing element 2000, e.g. of the housing body 2010. Additionally, or alternatively, the distal movement of the stabilizing element 2100 may occur until a proximal end of the ramp structure 2200 abuts the stabilizing body 2110, as will be described in detail further below.

The point at which the distal movement may stop is shown in the right portion of the schematic view of FIG. 3D. As can be seen, in this exemplary embodiment the ramp element 2020 may abut a portion of the stabilizing element 2100, thereby stopping the distal movement of the stabilizing element. This may be the second relative position of the stabilizing element 2100 with respect to the housing element 2000. At this point the circlip, which may be in its second state and engaged (e.g. more tightly) to the syringe in the circumferential gap, might be position at a proximal portion of the housing body 2010.

The circlip 2200, as mentioned, may be elastically deformable and would therefore tend to return to its first state, e.g. to a state with a wider diameter. The inner diameter of the housing body 2010 may correspond to the outer diameter of the circlip 2200 in its second state. This may hinder the circlip 2200 from returning to its first state. The circlip may therefore be held by the housing element, e.g. by the housing body in its second state. In other words, the circlip 2200, in its second state, once having passed the ramp structures 2200 may be radially constrained by the housing element 2000, e.g. by its inner walls. The housing element 2000 may be configured to hold the circlip in its second state when the stabilizing element 2100 is in the second relative position relative to the housing element The circlip 2200 may comprise a locked position in which it is arranged at the circumferential gap of the syringe 900 and held by the housing element 2000 in its second state. The circlip 2200 in its second state may be adapted to engage a surface of a distal portion of the medicament container 900, e.g. of the syringe 900, in order to prevent a relative movement of the medicament container 900 in at least one direction with respect to the circlip 2200, e.g. the axial direction.

As can be seen in FIG. 3D the syringe 900 may be moved further distally.

The syringe 900 may be moved further distally (as shown by the arrows in the figure) until the circlip 2200, e.g. the distal outer surface of the circlip 2200 abuts a proximal facing surface 2018, e.g. a circlip bearing surface 2018, of the housing element 2000. This may be a final position of the circlip 2200 and/or of the syringe 900 with respect to the housing element 2000.

The syringe 900 may therefore be confined in its further distal movement by the circlip 2200 being locked in the circumferential gap and abutting a proximal facing surface 2018 of a distal portion 2014 of the housing element 2000. The circlip 2200 may be distally offset from the stabilizing element 2100. The stabilizing element 2100 in its second relative position may be proximally offset to the viewing window of the drug delivery device 100.

An operational force acting on the syringe 900 would cause a movement of the syringe 900 with respect to the circlip 2200 if the circlip 2200 would not be held in its second state by the housing element 2000, e.g. if the circlip 2200 would have the possibility to return to its first state.

FIG. 3D, may therefore show a drug delivery device 100, which may comprise the assembly of any one of the previous described example, the device body 700; the medicament container, e.g. a syringe 900, comprising or adapted to comprise a medicament, e.g. the drug dr; the circlip 2200 configured, in a deformed state, e.g. its second state, to engage a surface of the medicament container 900 in order to prevent relative movement in at least one direction of the medicament container 900 with respect to the circlip; and the holding element, e.g. the housing element 2000, the holding element being configured to hold the circlip 2000 in its deformed state.

The flange of the syringe may be received in a proximal receiving portion of the stabilizing element 2100. The stabilizing element may be removed from the drug delivery device in some embodiments.

Figure 4:
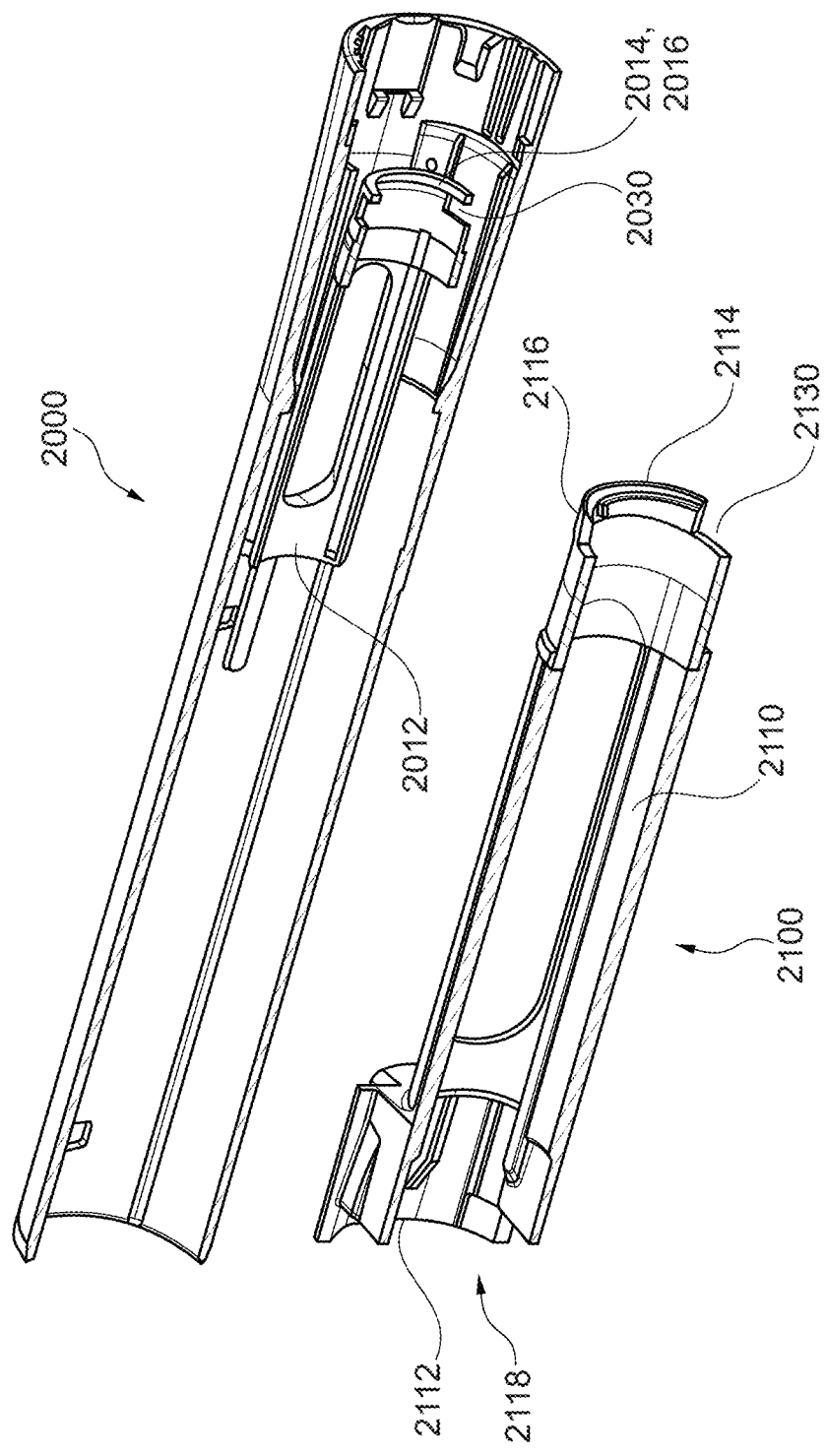

FIG. 4 shows a second exemplary embodiment of a housing element 2000 and a stabilizing element. This embodiment is similar to the one of FIGS. 2A to 2E. To avoid repetition, only the differences between the embodiments are described below. As regards to the other elements and features, which might not be explicitly mentioned here below, reference is made to the explanations given in the context of FIGS. 2A and 2E and 3A to 3D.

The housing element 2000 may comprise a distal end 2014. The housing element 2000 may comprise a proximal end 2012. The housing element 2000 may comprise a proximal end. The housing body 2010 of the housing element 2000 may extend from the proximal end 2012 to the distal end 2014. The housing element 2000 may be configured to be attached or integral to the device body 700 of the drug delivery device 100. A distal portion 2016 of the housing element 2000 may be configured to be arranged distally with respect to the viewing window 714 of the device body 100. The housing element 2000 may have a hollow cylindrical shape. The housing element 2000 may comprise a cut-out 2030 extending circumferentially and arranged proximal of the distal end 2014 of the housing element 200. In this embodiment the housing element 2000 does not comprise the ramp structures of the first embodiment. A part from the cut-out 2030 the distal end 2014 of the housing element 2000 is configured similarly than in the first embodiment, e.g. with the circlip bearing portion 2018.

In this example the stabilizing member 2100 may be configured as a syringe holder 2100. The embodiment is however not limited to a syringe holder 2100. The syringe holder 2100 may allow an accurate support of the syringe 900 during and after assembling. The stabilizing member 2100 may be adapted to assemble and hold the pre-filled syringe 900, e.g. a medicament container, within the device body 700 and is further explained in more detail in the following.

The stabilizing member 2100 may comprise a housing 2110, e.g. a stabilizing body 2110, adapted to receive the pre-filled syringe 900. The stabilizing member 2100 may comprise a rear end 2112, i.e. proximal end, opposite to the front end 2114. At the rear end 2112, the stabilizing member 2100 may comprise a flange portion 2130 that comprises clips 2120 for releasable intermittent holding of the stabilizing member 2100 relative to the device body 700.

The flange portion 2130 may form a receiving space 2118 into which a pre-filled syringe 900 is inserted distally into the hollow cylinder formed by a stabilizing body 2110.

The flange portion 2130 may be non-circular, e.g. comprising two rounded sections 2134 of the flange portion 2130 arranged oppositely, e.g. diametrically opposite, to each other and two in a radial inward direction recessed sections 2132 being flatter than the rounded sections 2134. As such the two rounded sections extend circumferentially as semi-circles. The two recessed sections may be arranged at the other opposite, e.g. diametrically opposite, ends of the flange portion 2130 and on opposite sides of the flange portion 2130 with respect to the rounded sections 2134. The two recessed sections 2132 may define a recessed outer flange surface.

Moreover, the stabilizing body 2110 may comprise at least one elongated window 2180 in order to enable visual inspection of the amount of drug Dr within pre-filled syringe 900 when syringe 900 is mounted within stabilizing member 2100. The stabilizing body 2110 may comprise the two elongated holder windows 2170 on sides that are opposite to each other.

A distal portion 2116 of the stabilizing element 2100 may have a greater inner diameter than a more proximal portion of the stabilizing body 2110. The distal portion 2116 of the stabilizing element 2100, may have a greater or equal outer diameter than a more proximal portion of the stabilizing body 2110.

The distal portion 2116 of the stabilizing element 2100 may be configured to be received in the housing element 2000. The distal portion 2116 of the stabilizing element 2100 may comprise an outer diameter which is smaller than the inner diameter of the housing body, e.g. of the housing body 2010 receiving the distal portion 2116 of the stabilizing element 2100.

The distal portion 2116 may be configured as a tilted surface 2170. The tilted surface 2170 may be configured to decrease in height in a distal direction as will become clear in the following figures.

The distal end of the stabilizing element 2100 may comprise a recess 2130, extending from the distal end 2014 proximally. The recess 2130 may be substantially the same size as the cut-out 2030 on the housing element.

FIGS. 5A to 5D shows, respectively, a cross section and a perspective view, of the housing element 200 and the stabilizing element 2100 of FIG. 4 and a medicament container 900, during assembly of a drug delivery device 100 according to a second exemplary embodiment. The left illustration in each figure show a cross section of the interaction between a medicament container 900, the housing element 2000, a circlip 2200 and the stabilizing element 2100. The right illustration in each Figure shows a perspective view of the interaction between a circlip 2200 and the housing element 2000. Reference will be made to a syringe 900, e.g. a pre-filled syringe. The disclosure however is not limited to this type of medicament container.

As can be seen in FIG. 5A, the circlip 2200 may be arranged at the distal portion of the housing element 2000. The circlip 2200 may be shaped as ring with open ends 2240 (see e.g. FIG. 2D). The radially outwardly facing surface of each end 2240 of the circlip 2200 may comprise an outwardly radially extending circlip protrusion 2242. In a first state of the circlip 2200, e.g. in a non-deformed state, the two open ends may be spaced apart from each other a first distance, e.g. a distances I1.

The cut-out 2030 of the housing element 2000 may be configured such that the two open ends 2240 of the circlip 2200 can be received in, e.g. may engage, the cut-out 2030, e.g. such that the two circlip protrusions 2242 can be received in the cut-out 2030 (see FIG. 5A right). In particular the cut-out may be dimensioned such that the two circlip protrusions 2242 can be received in the cut-out 2030 when the circlip is in its first state.

The circlip 2200 may have been inserted proximally into the housing body 2010, prior to the insertion of the syringe 900 and/or prior to the movement of the stabilizing element 2100. The circlip 2200 while being inserted may have to be rotationally aligned to the cut-out 2030 of the housing element 2000, such that the circlip protrusions 2242 are axially and radially aligned, e.g. substantially aligned with the cut-out 2030 of the housing element 2000.

In order to insert the circlip 2200 into the housing element 2000, the circlip 2200 may need to be deformed, e.g. the diameter may need to be decreased such as to fit the circlip 2200 into the housing body 2010. Without deforming the circlip 2200, the circlip 2200 may not fit inside the housing body 2010, e.g. due to the circlip protrusion 2242 which increase the radial width of the circlip 2200, e.g. greater than the inner diameter of the housing body 2010, or for example because it already had a wider diameter.

The circlip may be deformed such as to decrease the circlip's diameter. The distance between the circlip protrusions 2242 and/or the circlip arms 2240 may therefore be smaller than when the circlip 2200 is in its first state.

Once inserted, the circlip 2200 may then be moved distally until the distal end of the circlip 2214 abuts the distal end of the housing element 2000, e.g. a circlip bearing portion of the housing element. Additionally, or alternatively, the circlip 2200 may be moved distally until the circlip protrusions 2242 are aligned with the cut-out 2030 of the housing element 2000.

During the distal movement of the circlip 2200, the circlip 2200 may stay in its deformed position as it is radially constraint by the inner wall of the housing element 2000. At its final position, e.g. when the circlip 2200 abuts the distal end of the housing element 200 and/or when the circlip protrusions 2242 are aligned with the cut-outs, the circlip protrusions 2242 may be received in the cut-out 2030. The circlip 2200, at the distal end of the housing element 2000 may return to its first state, e.g. an undeformed state, due to the circlip protrusions 2242 being received in the cut-out 2030 and being free to extended circumferentially in the free space of the cut-out 2030. This may result in the circlip 2200 being free to expand to its first state.

The circlip 2200 may be fixedly positioned at its final position, e.g. may be radially and axially, e.g. at least distally, fix relative to the housing element. The fixed position may be given by the circlip protrusion 2242 engaging the cut-out 2030 of the housing element 2000 and the distal end of the housing element 2000 blocking any distal movement of the circlip 2200. Additionally or alternatively the housing element 2000 may comprise a groove into which the circlip may be received or arranged (not shown).

As can be seen in FIG. 5A, the stabilizing element 2100 may be inserted proximally into the housing element 2000. The stabilizing element 2100 may be moved distally into the housing element 2000. The stabilizing element 2100 may be rotationally aligned to the housing element 2000 and/or to the circlip 2200, such that the recess of the stabilizing element is aligned, e.g. circumferentially and axially, to the cut-out 2030 of the housing element 2000 and/or to the circlip protrusions 2242. The outer diameter of the stabilizing element may therefor be smaller than the inner diameter of the housing element 2000.

The stabilizing element 2100 may be moved into the housing element 2000 with or without a syringe 900 inserted into the stabilizing element 2100. First the stabilizing element 21000 may be inserted into the housing element 2000 and afterwards the syringe 900 into the stabilizing element 2100. Alternatively, first the syringe 900 may be received into the stabilizing element 2100 and afterwards the stabilizing element 2100 together with the syringe 900 may be inserted into the housing element 2000.

In cases where the stabilizing element 2100 is inserted into the housing element 2000 without the syringe 900, the stabilizing element 2100 may be pushed distally into the device body of the drug delivery device until the clip element 2120 of the stabilizing element 2100 (not shown)

engages a cut out 715 of the device body of the drug delivery device. The stabilizing element 2100 may therefore be axially (releasably) locked with respect to the device body 700 and/or with respect to the housing element 2000. In a locked position, the stabilizing element 2100 may be arranged in such away with respect to the housing element 2000 that a distal portion of the stabilizing element 2100 is already at least partially inserted into the housing element 2000 (e.g. into the hollow housing body 2010).

The syringe 900 may be inserted into the stabilizing element 2100. The syringe 900 may be moved distally with respect to the device body 700 of the drug delivery device 100 and/or with respect to the stabilizing element 2100 and/or with respect to the housing element 2000. The syringe 900 may be moved such that its rigid needle shield 914 passes into a through the circlip 2200.

In both cases, e.g. the syringe 900 being moved distally together with the stabilizing element 2100 or the syringe 900 being moved after the insertion of the stabilizing element 2100 has occurred, the distal movement of the syringe 900 relative to the housing element 2000 and/or to the circlip 2200 (and/or to the stabilizing element 2100), may stop once the circumferential gap 904 of the syringe 900 is aligned, e.g. radially aligned, with the circlip 2200.

Such a stop may be achieved via a stop element against which the syringe 900, e.g. a part of the syringe 900 abuts, thereby stopping its distal movement (not shown). Additionally, or alternatively when the syringe 900 and the stabilizing element 2100 are moved together distally into the housing element 2000, the locking of the stabilizing member to the device body 700, e.g. via the clip and the cut-out 715, may occur when the circumferential gap 904 and the circlip 2200 are aligned.

Additionally, or alternatively, a tool used to move the syringe 900 and/or the stabilizing element 2100 distally may comprise a stop element configured to abut an element of the drug delivery device such as to have the syringe 900, more specifically the circumferential gap 904 of the syringe aligned with the circlip 2200.

This may also be the final position of the syringe 900 with respect to the housing element 2000 and/or the device body 700.

The circlip 2200 may be in its first state, e.g. in its non-deformed state. The circlip 2200 may not be biased and as such, even if aligned to the circumferential gap 904 of the syringe 900, the circlip 2200 may not engage the circumferential gap 904 of the syringe 900 (as shown in FIG. 5A).

Figure 5B:
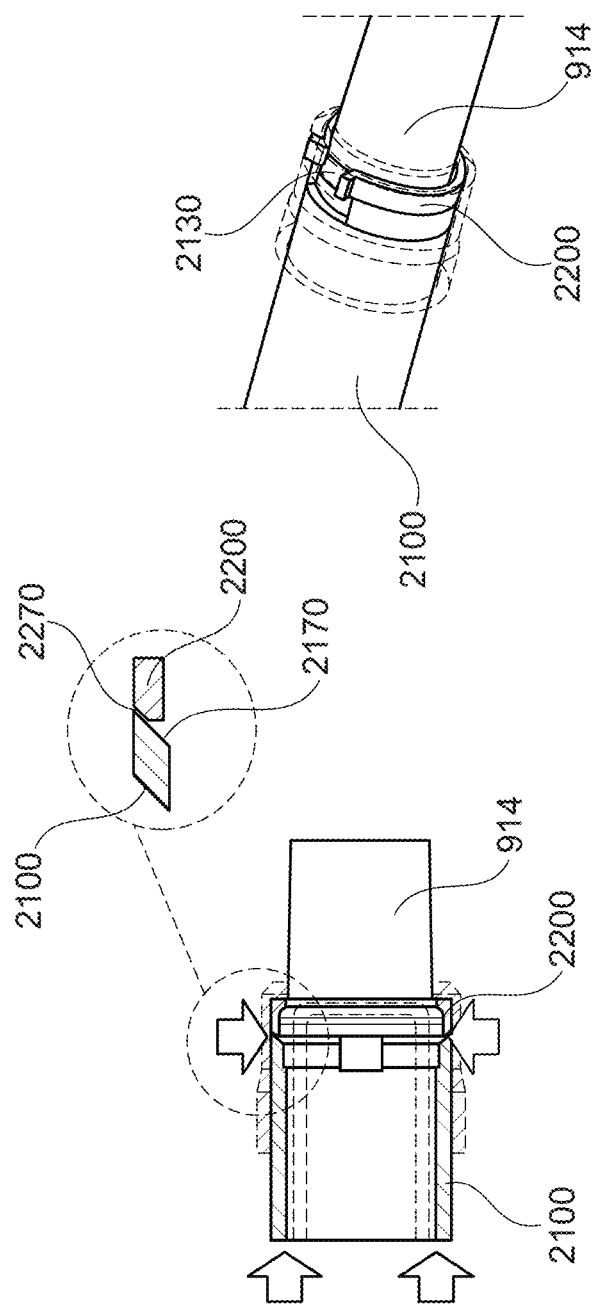

In a second step, as shown in FIG. 5B, the stabilizing element 2100 is moved distally with respect to the housing element 2000 and/or with respect to the circlip 2200 and/or with respect to the syringe 900.

The syringe 900 may be configured such that a distal movement of the stabilizing member 2100 does not cause a distal movement of the syringe 900 (which may be in its final axial position). This may for example be achieved through the stop element described in FIG. 5A.

As can be seen in the detailed view in FIG. 5B, the distal facing surface of the stabilizing element 2100 might comprise a tilted surface 2170 tilted in a distal and radially outward direction.

The proximal facing proximal surface of the circlip 2200 may also comprise a tilted section 2270 extending proximally and radially inwardly. The tilted section 2270 may have a tilt angle corresponding substantially to the tilt angle of the tilted surface 2170 of the stabilizing element 2100. The tilted section 2270 of the circlip 2200 may extend along the whole proximal facing surface of the proximal end 2214 of the circlip 2200 or extend only along a section of the proximally facing surface of the proximal end 2214 of the circlip 2200, e.g. along a section extending up to the radially outward end of the circlip 2200. In other words, the circlip may comprise at its proximal end, a proximally facing surface region of the proximally facing surface, wherein the proximally facing surface region might not be tilted. The proximally facing surface region not being tilted may be a region arranged more on the radially inwardly region of the proximally facing surface.

Figure 5C:
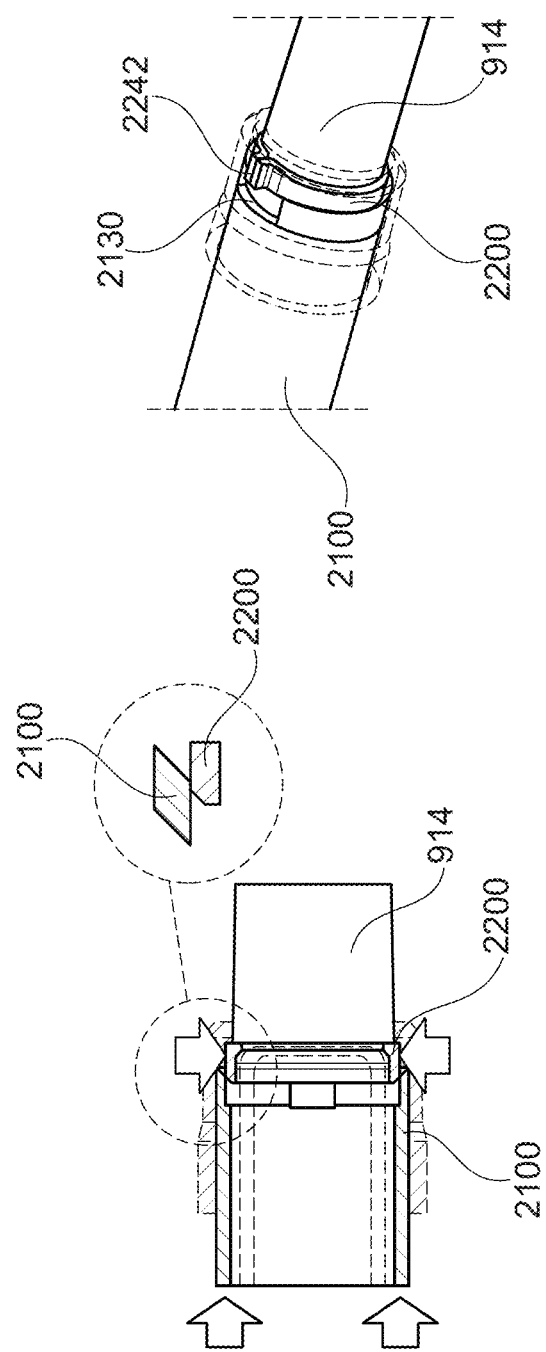

The tilted surface 2170 of the stabilizing element 2100 and the tilted section 2270 of the circlip 2200 may be configured such that a further distal move of the stabilizing element 2100 causes the circlip to deform in a radially inwardly direction as shown by the respective arrows (more in detail in FIG. 5C.

According to a further step, as shown in FIG. 5C the stabilizing element 2100 may be moved further distally (as shown by the arrows pointing in a distal direction). The tilted surface 2170 of the stabilizing element 2100 and the tilted section 2270 of the circlip 2200 may be configured such that an abutment of the tilted surface 2170 and of the tilted section 2270 and a distal movement of the stabilizing element 2100 with respect to the circlip 2200 (which may be blocked to move distally by the housing element 2000) causes the circlip 2200 to deform, e.g. in a radial inward direction (see e.g. the arrows pointing in a radially inwardly direction). This may correspond to the second state of the circlip 2200. In this state the ends 2240 of the circlip 2200 are abutting or nearly abutting each other. In other words, the distance between the open ends 2240 of the circlip 2200 in its second state is smaller than the distance of the open ends 2240 of the circlip 2200 in its first state.

The deformation of the circlip 2200 may cause the circlip 2200 to engage the circumferential gap 904 of the syringe 900. This may lead to the syringe 900 being secured, e.g. locked, by the circlip 2200 against any axial, e.g. distal, movement.

The stabilizing element 2100 may be moved further distally until its distal end 2114 abuts the housing element 2000, e.g. the proximally facing surface of the distal end of the housing element 2000 (see e.g. FIG. 5D).

As can be seen from the cross section view of FIG. 5D, a distal portion of the stabilizing element 2100 may be arranged radially between the housing element 2000 and the circlip 2200.

The protrusions 2242 of the circlip 2200 may be arranged at the cut-out 2030 of the housing element 2000 and/or of the stabilizing element 2100. The circlip 2200 is held in its second state by the inner walls of the stabilizing element 2100 and/or by the inner walls of the housing element 2000.

The circlip may now engage the syringe 900 in such a manner as described in relation to FIG. 3D, e.g. in relation to the forces that can be applied to the syringe. While in FIG. 3D the housing element 2000 may be or may comprises the holding element, in FIG. 5D it is the stabilizing element 2100 which may be or may comprise the holding element.

An operational force acting on the syringe 900 would cause a movement of the syringe 900 with respect to the circlip 2200 if the circlip 2200 would not be held in its second state by the stabilizing element 2000, e.g. if the circlip 2200 would have the possibility to return to its first state.

Figure 6B:
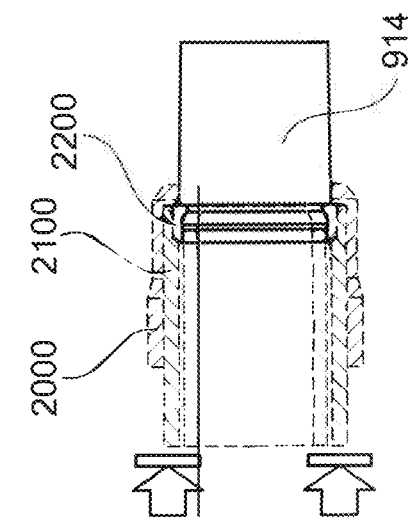
Figure 6D:
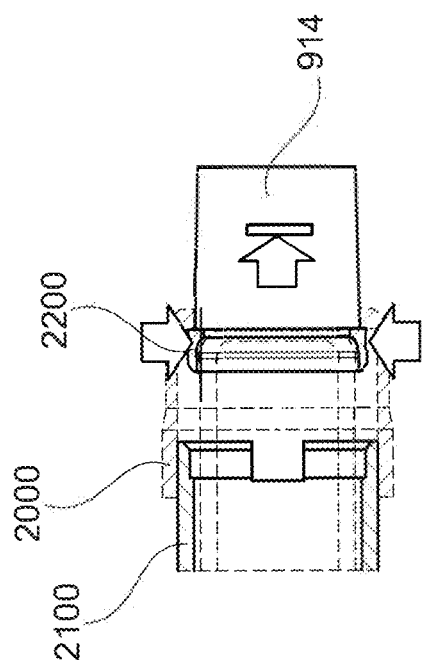
Figure 6A:
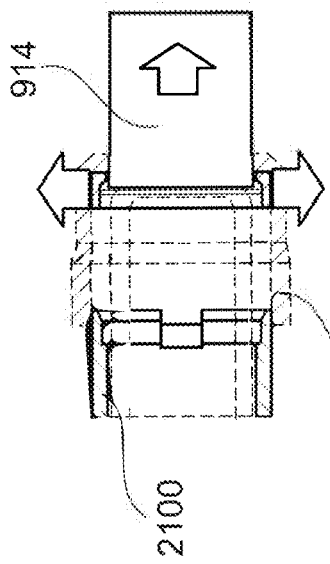
Figure 6C:
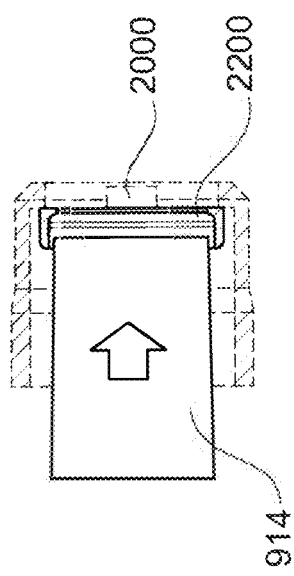

FIGS. 6A to 6C show a similar embodiment to the one in FIG. 5A to 5D, however with a different circlip 2200 and circlip arrangement. To avoid repetition, only the differences between the embodiments are described below. As regards to the other elements and features, which might not be explicitly mentioned here below, reference is made to the explanations given in the context of FIGS. 5A to 5D.

In the following embodiment, the circlip 2200 may be arranged at a distal end portion 2014 of the housing element 2000, e.g. abutting a circlip bearing portion of the housing element 2000. The circlip 2200 in this position may be in its second state, e.g. in a state with an outer diameter smaller than in the first state. The distal end portion of the housing element 2000 may be configured such as to permit a deformation of the circlip 2200 in a radially outwardly direction, e.g. a deformation in which the diameter of the circlip 2200 increases. The insertion of the circlip 2200 may be done as explained in relation to FIGS. 5A to 5D.

The distal end portion of the housing element 2000 may comprise a groove, e.g. an annular groove. The circlip 2200 may be configured to be fixed in its axial position with respect to the housing element 2000 by the groove.

The syringe 900 may then be inserted into proximally into the housing element 2000. The syringe 900 may already be inserted into the stabilizing element 2100. Together they may be inserted into the device body 700 of the drug delivery device 100. The description with regards to the stabilizing element 2100 of FIG. 5A to 5D also holds for this embodiment.

The interaction between the syringe 900 and the circlip 2200 may however be different than in the previous embodiment.

When the syringe 900 is moved distally into the housing element 2000, the distal end of the rigid needle shield may contact the circlip 2200, e.g. in its second state. The circlip 2200 in its second state may have an inner diameter being smaller than the outer diameter of the rigid needle shield 914. When the rigid needle shield 914 passes the circlip 2200, the circlip 2200 may then be deformed in a deformed state with a diameter being greater than in the second state as shown by the radially outwardly pointing arrows. This may correspond to the first state of the circlip 2200. This is for example shown in FIG. 6B. The radially outwardly deformation of the circlip 2200 occurs as described for example in FIG. 3A. The first prime state described in FIG. 3A may represent the first state in the embodiment of FIG. 6B.

Before alignment occurs, the circlip 2200 may still be biased towards its second state, e.g. the circlip 2200 may be in its state with a wider diameter but would tend to return to its second state with the narrower diameter.

As shown in FIG. 6C, once alignment with the circumferential gap 904 occurs, the circlip 2200 might return to its second state, e.g. by deforming radially inwardly, as shown by the respective arrows pointing radially inward. The circlip 2200 may return to its second state and be received in the circumferential gap 904. The distal facing surface of the circlip 2200 may abut the rigid needle shield. The contoured surface may be such as to engage at least partially the contour of the barrel 901 of the syringe 900. The circlip 2200 may therefore be engaged to the syringe 900.

The engagement of the circlip to the syringe 900 may be such that an operation force applied on the syringe during operation of the drug delivery device, would result in a disengagement of the circlip to the syringe, e.g. in an axial move of the syringe relative to the circlip 2200.

According to a further step, as shown in FIG. 6D the stabilizing element 2100 may be moved further distally (as shown by the arrows pointing in a distal direction) without deforming the circlip 2200.

The tilted surface 2170 of the stabilizing element 2100 and the tilted section 2270 of the proximal end of the circlip 2200 may be configured such that the distal end portion of the stabilizing element 2100 may be arranged between the inner wall of the housing element 2000 and the outer wall of the circlip 2200 thereby preventing any radial movement and/or radial deformation of the circlip 2200 in an outward direction.

This may lead to the syringe 900 being secured, e.g. locked, by the circlip 2200 against any axial, e.g. distal, movement.

Alternatively, the stabilizing element 2100 may be moved further distally (as shown by the arrows pointing in a distal direction). The tilted surface 2170 of the stabilizing element 2100 and the tilted section 2270 of the circlip 2200 may be configured such that an abutment of the tilted surface 2170 and of the tilted section 2270 and a distal movement of the stabilizing element 2100 with respect to the circlip 2200 (which may be blocked to move distally by the housing element 2000) causes the circlip 2200 to further deform, e.g. in a radial inward direction. This may correspond to a second prime state of the circlip 2200. In this state the end 2240 of the circlip 2200 are abutting or nearly abutting each other. In other words, the distance between the open ends 2240 the circlip 2200 in its second state is smaller than the distance of the open ends 2240 of the circlip 2200 in its first state and/or in its second state.

The deformation of the circlip 2200 may cause the circlip 2200 to engage the circumferential gap 904 of the syringe 900 even stronger. This may lead to the syringe 900 being secured, e.g. locked, by the circlip 2200 against any axial, e.g. distal, movement.

The stabilizing element 2100 may be moved further distally until its distal end 2114 abuts the housing element 2000, e.g. the proximally facing surface of the distal end of the housing element 2000.

As can be seen from the cross section view of FIG. 6D, a distal portion of the stabilizing element 2100 may be arranged radially between the housing element 2000 and the circlip 2200.

In both cases an operation force acting on the syringe 900 would cause a movement of the syringe 900 with respect to the circlip 2200 if the circlip 2200 would not be held in its second state or second prime state by the stabilizing element 2000, e.g. if the circlip 2200 would have the possibility to return to its first state.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrome.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, small modular immunopharmaceuticals (SMIP), binding-domain immunoglobulin fusion proteins, camelized antibodies, and immunoglobulin single variable domains. Additional examples of antigen-binding antibody fragments are known in the art.

The term "immunoglobulin single variable domain" (ISV), interchangeably used with "single variable domain", defines immunoglobulin molecules wherein the antigen binding site is present on, and formed by, a single immunoglobulin domain. As such, immunoglobulin single variable domains are capable of specifically binding to an epitope of the antigen without pairing with an additional immunoglobulin variable domain. The binding site of an immunoglobulin single variable domain is formed by a single heavy chain variable domain (VH domain or VHH domain) or a single light chain variable domain (VL domain). Hence, the antigen binding site of an immunoglobulin single variable domain is formed by no more than three CDRs.

An immunoglobulin single variable domain (ISV) can be a heavy chain ISV, such as a VH (derived from a conventional four-chain antibody), or VHH (derived from a heavy-chain antibody), including a camelized VH or humanized VHH. For example, the immunoglobulin single variable domain may be a (single) domain antibody, a "dAb" or dAb or a Nanobody® ISV (such as a VHH, including a humanized VHH or camelized VH) or a suitable fragment thereof. [Note: Nanobody® is a registered trademark of Ablynx N.V.]; other single variable domains, or any suitable fragment of any one thereof.

"VHH domains", also known as VHHs, VHH antibody fragments, and VHH antibodies, have originally been described as the antigen binding immunoglobulin variable domain of "heavy chain antibodies" (i.e., of "antibodies devoid of light chains"; Hamers-Casterman et al. 1993 (Nature 363: 446-448). The term "VHH domain" has been chosen in order to distinguish these variable domains from the heavy chain variable domains that are present in conventional 4-chain antibodies (which are referred to herein as "VH domains") and from the light chain variable domains that are present in conventional 4-chain antibodies (which are referred to herein as "VL domains"). For a further description of VHH's, reference is made to the review article by Muyldermans 2001 (Reviews in Molecular Biotechnology 74: 277-302).

For the term "dAb's" and "domain antibody", reference is for example made to Ward et al. 1989 (Nature 341: 544), to Holt et al. 2003 (Trends Biotechnol. 21: 484); as well as to WO 2004/068820, WO 2006/030220, WO 2006/003388. It should also be noted that, although less preferred in the context of the present invention because they are not of mammalian origin, single variable domains can be derived from certain species of shark (for example, the so-called "IgNAR domains", see for example WO 2005/18629).

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

REFERENCE LIST

- 100 drug delivery device
- 101 drive mechanism
- 200 cap
- 500 needle cover
- 501 skin contact surface
- 700 device body
- 719 viewing window
- 714 cut-out
- 715 cut-out
- 900 medicament container/syringe
- 901 barrel
- 904 circumferential gap
- 908 needle
- 912 flange
- 914 needle shield
- 1000 plunger
- 2000 housing element/holding element
- 2010 body of housing element
- 2012 proximal end
- 2014 distal end
- 2016 distal portion
- 2018 receiving space
- 2020 interface feature/ramp structure
- 2022 proximal end ramp structure
- 2030 cut-out
- 2040 abutment surface
- 2070 tilted section
- 2100 stabilizing element/syringe carrier
- 2110 body
- 2112 proximal end stabilizing element
- 2114 distal end stabilizing element
- 2116 distal portion
- 2118 receiving space
- 2120 holding clip
- 2130 recess
- 2132 flat section
- 2134 rounded sections
- 2142 circlip receptacle delimiting members
- 2144 circlip holding arms
- 2146 circlip holding arms protrusion
- 2148 slot
- 2150 circlip receptacle
- 2160 alignment features
- 2170 tilted surface
- 2200 circlip
- 2212 proximal end
- 2214 distal end
- 2232 distal facing surface
- 2234 contoured surface
- 2240 open ends
- 2242 circlip protrusion
- d1 proximal diameter
- d2 inner diameter
- d3 inner diameter distal end
- d2100_a proximal diameter
- d2100_b distal diameter
- d2100_c minimal diameter
- d2200_a first inner diameter
- d2200_b second inner diameter
- d2200_c first outer diameter receiving space
- d2200_d second outer diameter
- w2200 width circlip
- l1 distance between circlip arms

The invention claimed is:

1. A drug delivery device comprising:
an assembly comprising a circlip, a stabilizing element, and a housing element;
a device body; and
a medicament container comprising or adapted to comprise a medicament,
wherein the circlip is configured to assume a first state and a deformed state,
wherein the stabilizing element is configured to radially stabilize the medicament container and the housing element is adapted to receive at least a portion of the medicament container,
wherein the stabilizing element comprises a circlip receptacle configured to receive the circlip in the first state when the stabilizing element is in a first position relative to the housing element,
wherein the circlip receptacle is configured such that an axial relative movement between the circlip in the first state and the stabilizing element is restrained,
wherein the stabilizing element and the housing element are configured such that an axial relative movement of the stabilizing element from the first position relative to the housing element into a second position relative to the housing element causes the circlip to assume the deformed state,
wherein in the deformed state, the circlip is adapted to engage a surface of the medicament container in order to prevent a relative movement of the medicament container in at least one direction with respect to the circlip, and
wherein the housing element is configured to hold the circlip in the deformed state.

2. The drug delivery device according to claim 1, wherein the circlip is configured to abut a proximal facing surface of a distal end of the housing element.

3. The drug delivery device according to claim 1, wherein the housing element is configured to radially retain the circlip in the deformed state to prevent an axial movement of the medicament container relative to the circlip when an axial force is applied to the medicament container when the circlip is in the deformed state.

4. The drug delivery device according to claim 1, wherein an inner diameter of a distal end of the housing element is smaller than an outer diameter of the circlip in the deformed state, and/or wherein an inner diameter of a portion of housing element proximal to the distal end of the housing element is greater than the inner diameter of the distal end of the housing element and/or smaller than the outer diameter of the circlip in a non-deformed state.

5. The drug delivery device according to claim 1, further comprising a viewing window, wherein the housing element extends further distally than the viewing window and/or wherein the housing element extends further proximally than the viewing window.

6. An assembly for a drug delivery device, the assembly comprising:
   a circlip;
   a stabilizing element; and
   a housing element,
   wherein the circlip is configured to assume a first state and a second state, wherein in the second state, a diameter of the circlip is smaller than in the first state,
   wherein the stabilizing element is configured to radially stabilize a medicament container and the housing element is adapted to receive at least a portion of the medicament container,
   wherein the stabilizing element comprises a circlip receptacle configured to receive the circlip in the first state when the stabilizing element is in a first position relative to the housing element,
   wherein the circlip receptacle is configured such that an axial relative movement between the circlip in the first state and the stabilizing element is restrained,
   wherein the stabilizing element and the housing element are configured such that an axial relative movement of the stabilizing element from the first position relative to the housing element into a second position relative to the housing element causes the circlip to assume the second state,
   wherein the circlip in the second state is adapted to engage a surface of a distal portion of the medicament container in order to prevent a relative movement of the medicament container in at least one direction with respect to the circlip, and
   wherein the housing element is configured to radially restrain the circlip when the circlip is in the second state.

7. The assembly of claim 6, wherein the second state of the circlip is a deformed state of the circlip.

8. The assembly according to claim 6, wherein the stabilizing element comprises at least one circlip restraining feature configured to restrain the axial relative movement between the circlip in the first state and the stabilizing element, when the circlip is received in the circlip receptacle.

9. The assembly according to claim 6, further comprising an interface feature, wherein when the stabilizing element changes from the first position relative to the housing element to the second position relative to the housing element, the interface feature is configured to interact with the circlip to bring the circlip from the first state to the second state; and/or
   wherein the interface feature is in the housing element, wherein the interface feature is configured as a ramp structure, wherein the circlip receptacle comprises at least one slot, and wherein the at least one slot is configured to receive the ramp structure thereby bringing the circlip from the first state to the second state when the stabilizing element moves from the first position relative to the housing element to the second position relative to the housing element.

10. A method of assembling a drug delivery device, the method comprising:
    axially sliding a medicament container into a circlip,
    radially stabilizing the medicament container using a stabilizing element of the drug delivery device, wherein the stabilizing element comprises a circlip receptacle configured to receive the circlip in a first state when the stabilizing element is in a first position relative to a housing element of the drug delivery device, wherein the housing element is adapted to receive at least a portion of the medicament container,
    arranging the stabilizing element and the housing element such that an axial movement of the stabilizing element from a first position relative to the housing element into a second position relative to the housing element causes the circlip to assume a second state,
    wherein in the second state, the circlip engages an axial stop surface of the medicament container to prevent a movement of the medicament container relative to the circlip in at least one direction, and
    arranging the circlip and the medicament container relative to the housing element such that the circlip is retained in the second state via the housing element, and
    wherein the circlip receptacle is configured such that an axial relative movement between the circlip in the first state and the stabilizing element is restrained.

11. The method of claim 10, wherein a diameter of the circlip is smaller in the second state than in the first state.

12. The method of claim 10, wherein the second state of the circlip is a deformed state of the circlip.

13. The method of claim 10, wherein the circlip is retained in the second state via the housing element to prevent an axial movement of the medicament container relative to the circlip when an axial force is applied to the medicament container.

14. The method of claim 10, wherein the drug delivery device comprises a viewing window, and wherein the method further comprises arranging the housing element such that the housing element extends further distally than the viewing window and/or the housing element extends further proximally than the viewing window.

\* \* \* \* \*